(12) United States Patent
Levchik et al.

(10) Patent No.: US 9,321,719 B2
(45) Date of Patent: Apr. 26, 2016

(54) CRYSTALLINE POLYMORPHIC FORMS OF MONOSODIUM N-[-8-(2-HYDROXYBENZOYL)AMINO]CAPRYLATE

(71) Applicant: Emisphere Technologies, Inc., Roseland, NJ (US)

(72) Inventors: Halina Levchik, Croton On Hudson, NY (US); Shingai Majuru, Brewster, NY (US); Brahma Singh, Jamaica, NY (US); Jamila Harris, Flushing, NY (US)

(73) Assignee: EMISPHERE TECHNOLOGIES, INC., Roseland, NJ (US)

( * ) Notice: Subject to any disclaimer, the term of this patent is extended or adjusted under 35 U.S.C. 154(b) by 37 days.

(21) Appl. No.: 14/138,787

(22) Filed: Dec. 23, 2013

(65) Prior Publication Data

US 2014/0187813 A1    Jul. 3, 2014

Related U.S. Application Data

(63) Continuation of application No. 11/568,783, filed as application No. PCT/US2005/016126 on May 6, 2005, now Pat. No. 8,636,996.

(60) Provisional application No. 60/569,476, filed on May 6, 2004, provisional application No. 60/619,418, filed on Oct. 15, 2004.

(51) Int. Cl.
 *C07C 235/60* (2006.01)

(52) U.S. Cl.
 CPC .................................. *C07C 235/60* (2013.01)

(58) Field of Classification Search
 None
 See application file for complete search history.

(56) References Cited

U.S. PATENT DOCUMENTS

| | | | |
|---|---|---|---|
| 5,866,536 | A | 2/1999 | Leone-Bay et al. |
| 2002/0065255 | A1 | 5/2002 | Bay et al. |

FOREIGN PATENT DOCUMENTS

| | | |
|---|---|---|
| WO | WO-9630036 A1 | 10/1996 |
| WO | WO-0059863 A1 | 10/2000 |

OTHER PUBLICATIONS

Baughman, et al., Circulation, 1998, 98, pp. 1610-1615.
Brittain, et al., Polymorphism in Pharmaceutical Solids, vol. 95, 1999, 348-361.
Brittain, H.G. (Editor), Polymorphism in Pharmaceutical Solids, Marcel dekker, Inc., (1999), pp. 2 and 141-1163.
US Pharmacopia #23, National Formulary #18, 1995, p. 1843-1844.

*Primary Examiner* — Kamal Saeed
(74) *Attorney, Agent, or Firm* — Blank Rome LLP

(57) ABSTRACT

The present invention relates to crystalline polymorphic forms of monosodium N-[8-(2-hydroxybenzoyl)amino]caprylate ("SNAC"), including two hydrates, a methanol solvate, and an ethanol solvate, of SNAC. More specifically, the present invention provide six polymorphic forms of SNAC (hereafter referred to as Forms I-VI). The present invention also provides an amorphous form of SNAC.

19 Claims, 45 Drawing Sheets

XRPD scan of anydrate (Form I) SNAC

FTIR spectrum of Form II of SNAC.

Moisture sorption/desorption profile of Form II of SNAC.

XRPD scan of Form II of SNAC

TGA scan of FormII of SNAC

FTIR spectrum of FormII of SNAC.

XRPD an of Form III SNAC

DSC scan of Form III of SNAC

FTIR spectrum of Form V of SNAC.

Moisture sorption/desorption profile of Form V of SNAC (not pre-dried sample).

XRPD scan of Form IV of SNAC

DSC scan of Form IV of SNAC.

TGA scan of Form IV of SNAC.

FTIR spectrum of Form IV of SNAC

Moisture sorption/desorption of Form IV of SNAC.

PXRD scan of Form V of SNAC

TGA scan of Form V of SNAC.

FTIR spectrum of Form V of SNAC.

Moisture sorption/desorption profile of Form V of SNAC (not pre-dried sample).

XRPD scan of Form VI of SNAC

DSC scan of Form VI of SNAC.

TGA scan of Form IV of SNAC.

FT-IR spectrum of Form VI (EtOH/H₂O co-solvate) of SNAC

Moisture sorption/desorption pofile of Form VI of SNAC.

Effect of Bail Milling on XRPD pattern of Form I

Effect of Wet Granulation on XRPD pattern of Form I

Effect of Compression on XRPD pattern of Form I

Effect of Compression on XRPD pattern of Form III

XRPD scan of Amorphous Form containing Approx. 10% of Form III

DSC scan of Amorphous Form containing Approx. 10% of Form III

TGA scan of Amorphous Form containing Approx. 10% of Form III

CRYSTALLINE POLYMORPHIC FORMS OF MONOSODIUM N-[-8-(2-HYDROXYBENZOYL)AMINO]CAPRYLATE

This application is a continuation of U.S. patent application Ser. No. 11/568,753, filed Sep. 22, 2008, which is a national phase of International Patent Application No. PCT/US2005/016126, filed May 6, 2005, which was published in English as International Publication No. WO2005/107462 and claims the benefit of U.S. Provisional Application No. 60/569,476, filed May 6, 2004, and U.S. Provisional Application No. 60/619,418, filed Oct. 15, 2004, both of which are hereby incorporated by reference.

FIELD OF THE INVENTION

The present invention relates to crystalline polymorphic forms of monosodium N-[8-(2-hydroxybenzoyl)amino]caprylate, amorphous monosodium N-[8-(2-hydroxybenzoyl)amino]caprylate, pharmaceutical compositions containing the same, methods of preparing the same, and methods for facilitating the delivery of active agents with the same.

BACKGROUND OF THE INVENTION

U.S. Pat. No. 5,650,386 discloses N-[8-(2-hydroxybenzoyl)amino]caprylic acid and salts thereof, and their use for facilitating the delivery of various active agents.

SUMMARY OF THE INVENTION

The present invention relates to polymorphic forms of monosodium N-[8-(2-hydroxybenzoyl)amino] caprylate ("SNAC"), including two hydrates, a methanol/water co-solvate, and an ethanol/water co-solvate, of SNAC. More specifically, the present invention provides six polymorphic forms of SNAC (hereafter referred to as Forms I-VI). The present invention also provides an amorphous form of SNAC.

One embodiment of the invention is a pharmaceutical composition comprising (A) (i) one or more of Forms I-VI of SNAC and/or (ii) amorphous SNAC, and (B) an active agent, such as heparin. According to a preferred embodiment, the pharmaceutical composition comprises at least about 20, 30, 40, 50, 60, 70, 80, 90, 95, 96, 97, 98, 99, 99.1, 99.2, 99.3, 99.4, 99.5, 99.6, 99.7, 99.8, or 99.9% by weight of one of Forms I-VI of SNAC or amorphous SNAC, based upon 100% total weight of SNAC in the pharmaceutical composition. According to another preferred embodiment, the pharmaceutical composition comprises at least about 20, 30, 40, 50, 60, 70, 80, 90, 95, 96, 97, 98, 99, 99.1, 99.2, 99.3, 99.4, 99.5, 99.6, 99.7, 99.8, or 99.9% by weight of one of Forms I-VI of SNAC, based upon 100% total weight of crystalline SNAC in the pharmaceutical composition.

Yet another embodiment of the invention is a method for administering or facilitating the delivery of an active agent in an animal (such as a human) by administering the pharmaceutical composition of the present invention.

Yet another embodiment is a method of treating thrombosis in an animal (such as a human) in need thereof by orally administering an anti-thrombosis effective amount of the pharmaceutical composition of the present invention comprising heparin.

Yet another embodiment is a method of preparing Form I of SNAC comprising the step of heating Form III, V, or VI of SNAC or a mixture thereof to at least 50° C. (but preferably less than 110° C.) for a time sufficient to form Form I of SNAC.

Yet another embodiment is a method of preparing Form I of SNAC comprising the step of heating amorphous SNAC at from about 30 to about 90° C., and preferably from about 40 to about 80° C., for a time sufficient to form Form I of SNAC.

Yet another embodiment is a method of preparing Form I of SNAC comprising the step of lyophilizing any form of SNAC other than Form I to yield Form I. For example, the method can include lyophilizing one or more of Forms II-VI of SNAC and/or amorphous SNAC to yield Form I.

Yet another embodiment is a pharmaceutical composition, such as a tablet, comprising a milled (e.g., ball milled) or directly compressed mixture of Form I of SNAC and at least one active agent and/or pharmaceutically acceptable additive (such as those described below). The pharmaceutical composition can be prepared by milling (e.g., ball milling) or compression (e.g., direct compression) of a mixture of Form I of SNAC and at least one active agent and/or pharmaceutically acceptable additive.

Yet another embodiment is a method of preparing Form II of SNAC comprising the step of drying (e.g., tumble drying) a solvate (e.g., an ethanol solvate or methanol solvate) of SNAC without agitation and exposing the dried SNAC to moisture for a sufficient time to yield Form II of SNAC. Preferably, the drying and exposure steps are performed in a closed container. The dried SNAC may be stored in a moist environment to cause conversion of any remaining SNAC, which is not Form II SNAC, to Form II.

Yet another embodiment is a pharmaceutical composition, such as a tablet, comprising a directly compressed mixture of Form II of SNAC and at least one active agent and/or pharmaceutically acceptable additive (such as those described below). The pharmaceutical composition can be prepared by compression (e.g., direct compression) of a mixture of Form II of SNAC and at least one active agent and/or pharmaceutically acceptable additive.

Yet another embodiment is a method of preparing Form III of SNAC comprising the step of exposing Form I, II, IV, V, or VI of SNAC or a mixture thereof to an environment having a relative humidity of 75%, 80%, 85%, 90%, or greater, for a sufficient time to yield Form III.

Yet another embodiment is a method of preparing Form III of SNAC comprising the step of exposing amorphous SNAC to moisture (i.e., an environment having a relative humidity greater than 0% and preferably greater than 5 or 10%) for a sufficient time to yield Form III.

Yet another embodiment is a method of preparing Form III of SNAC comprising the step of wet granulating Form I, II, IV, V, or VI of SNAC or amorphous SNAC or a mixture thereof (with or without one or more active agents and/or pharmaceutically acceptable additives (such as those described below)) for a sufficient time to produce Form III. According to one embodiment, Form I of SNAC is wet granulated.

Yet another embodiment is a method of preparing Form III of SNAC comprising the step of exposing Form V or VI of SNAC or a mixture thereof to an environment having a relative humidity of 30%, 35%, 40%, 50% or greater, for a sufficient time to yield Form III.

Yet another embodiment is a method of preparing Form III of SNAC comprising the step of exposing Form VI of SNAC to an environment having a relative humidity of 10%, 20%, 30% or greater, for a sufficient time to yield Form III.

Yet another embodiment is a method of preparing Form III of SNAC comprising the step of crystallizing SNAC from water.

Yet another embodiment is a method of preparing Form III of SNAC comprising the step of wet granulating Form I of SNAC for a sufficient time to produce Form III.

Yet another embodiment is a pharmaceutical composition, such as a tablet, comprising a directly compressed mixture of Form III of SNAC and at least one active agent and/or pharmaceutically acceptable additive (such as those described below). The pharmaceutical composition can be prepared by compression (e.g., direct compression) of a mixture of Form III of SNAC and at least one active agent and/or pharmaceutically acceptable additive.

Yet another embodiment is a method of preparing Form IV of SNAC comprising the step of heating Form I, II, III, V, or VI of SNAC or a mixture thereof to a temperature between about 110 or 150° C. and the melting point of SNAC (e.g., at 150 or 170° C.) for a sufficient time to yield Form IV.

Yet another embodiment is a method of preparing Form V of SNAC comprising the step of crystallizing SNAC from a methanol solution at a relative humidity of at least 30, 40, or 50%. Preferably, the methanol is substantially or completely free of water. Without being bound by any particular theory, it is believed that the methanol solvate exchanges methanol for atmospheric water over time resulting in the methanol-water solvate of Form V. For example, Form V may be prepared by preparing a saturated solution of SNAC (e.g., Form I-IV or VI of SNAC or a mixture thereof) in methanol at a relative humidity of at least 30, 40, or 50%, and cooling the solution, e.g., to room temperature or lower (such as in an ice bath). The resulting precipitate can be filtered and dried.

Yet another embodiment is a method of preparing Form V of SNAC comprising the step of equilibration of Forms I-IV or VI of SNAC with methanol. Preferably, the methanol solution is substantially or completely free of water. For example, Form V can be prepared by slurring any of Forms I-IV or VI or a mixture thereof in methanol at a relative humidity of at least 30, 40, or 50%, and maintaining the slurried mixture at ambient temperatures for a sufficient time to form Form V (e.g., several days).

Yet another embodiment is a method of preparing Form VI of SNAC comprising the step of crystallizing SNAC from an ethanol solution at a relative humidity of at least 30, 40 or 50%. Preferably, the ethanol solution is substantially or completely free of water. For example, Form VI can be prepared by preparing a saturated solution of SNAC (e.g., Form I-V of SNAC or a mixture thereof) in ethanol at a relative humidity of at least about 30, 40, or 50% and cooling the solution to room temperature or lower.

Yet another embodiment is a method of preparing Form VI of SNAC comprising the step of slurring any of Forms I-V in ethanol at a relative humidity of at least 10, 20, or 30%. Preferably, the ethanol is substantially or completely free of water. For example, Form VI can be prepared by adding any of Forms I-V to ethanol to form a precipitate, and maintaining the slurried mixture at ambient temperatures for a sufficient time to form Form VI.

Yet another embodiment is a method of preparing amorphous SNAC by dehydrating Form III of SNAC (e.g., in a vacuum) for a sufficient time to form amorphous SNAC.

DETAILED DESCRIPTION OF THE INVENTION

Definitions

Figure 1:
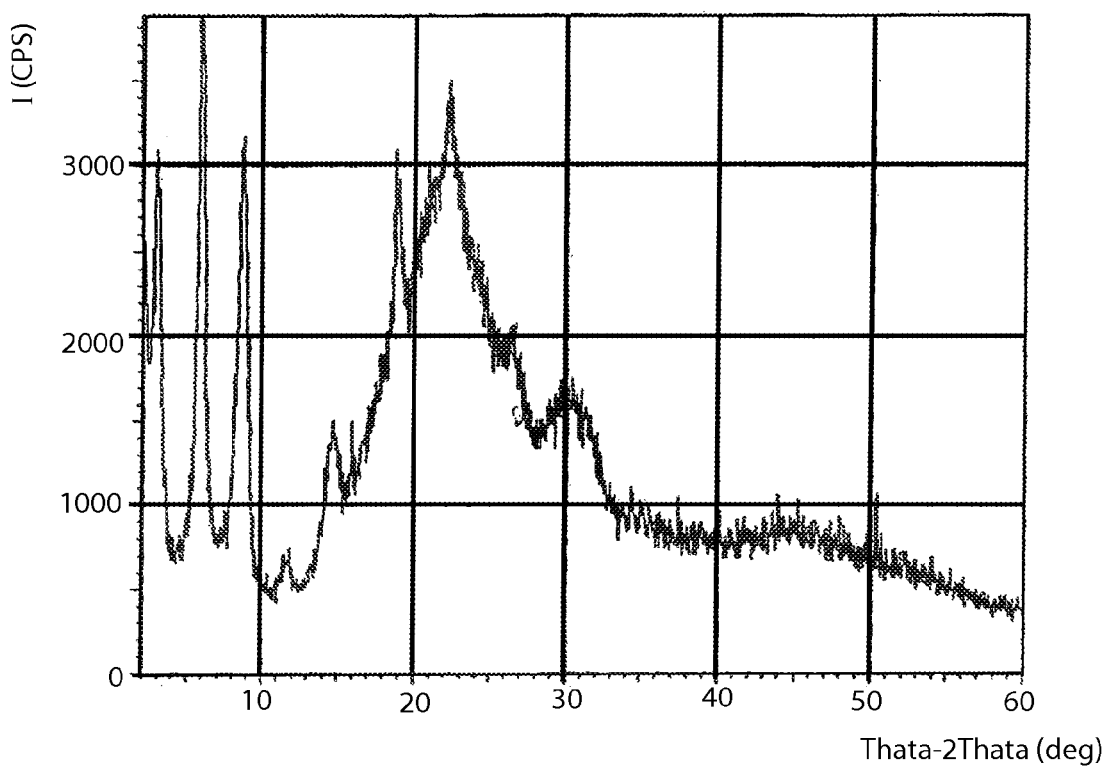
FIGS. 1, 6, 11, 16, 21, 26, and 43 are X-ray powder diffractograms (XRPDs) of Forms I-VI of SNAC and amorphous SNAC (containing approximately 10% Form III of SNAC), respectively, as prepared in Examples 1-6 and 14.

The term "polymorph" refers to crystallographically distinct forms of a substance.

The term "hydrate" as used herein includes, but is not limited to, (i) a substance containing water combined in the molecular form and (ii) a crystalline substance containing one or more molecules of water of crystallization or a crystalline material containing free water.

The term "SNAC" as used herein refers to monosodium N-[8-(2-hydroxybenzoyl)amino] caprylate. Unless otherwise noted, the term "SNAC" as used herein refers to all polymorphs of SNAC.

The term "SNAC 1/3 hydrate" as used herein refers to a crystalline form of SNAC in which one molecule of water is associated with three molecules of SNAC.

The term "SNAC trihydrate" as used herein refers to a crystalline form of SNAC in which three molecules of water are associated with each molecule of SNAC.

The term "solvate" as used herein includes, but is not limited to, a molecular or ionic complex of molecules or ions of a solvent with molecules or ions of SNAC. The term "co-solvate" as used herein includes, but is not limited to, a molecular or ionic complex of molecules or ions of two or more solvents with molecules or ions of SNAC.

The term "delivery agent" as used herein refers to SNAC, including its crystalline polymorphic forms.

An "effective amount of drug" is an amount of the active agent (e.g., heparin) which is effective to treat or prevent a condition in a living organism to whom it is administered over some period of time, e.g., provides a therapeutic effect during a desired dosing interval. Effective doses will vary, as recognized by those skilled in the art, depending on the route of administration, excipient usage, and the possibility of co-usage with other agents for treating a condition.

The term "treat", "treating", or "treated" refers to administering an active agent with the purpose to cure, heal, alleviate, relieve, alter, remedy, ameliorate, improve, or affect a condition (e.g., a disease), the symptoms of the condition, or the predisposition toward the condition.

An "effective amount of delivery agent" is an amount of the delivery agent which promotes the absorption of a desired amount of the active agent via any route of administration (such as those discussed in this application including, but not limited to, the oral (e.g., across a biological membrane in the gastrointestinal tract), nasal, pulmonary, dermal, vaginal, and/or ocular route).

The term "heparin" as used herein refers to all forms of heparin, including, but not limited to, unfractionated heparin, heparinoids, dermatans, chondroitins, low molecular weight heparin (e.g., tinzaparin (including tinzaparin sodium)), very low molecular weight heparin, and ultra low molecular weight heparin. A preferred type of heparin is unfractionated heparin, such as heparin sodium (e.g., heparin sodium USP). The term "low molecular weight heparin" generally refers to heparin in which at least 80% (by weight) of the heparin has a molecular weight of between about 3000 and about 9000 daltons. Non-limiting examples of low molecular weight heparin include tinzaparin, enoxaprin, and daltiparin. Tinzaparin has been approved by the FDA for the treatment of acute symptomatic deep vein thrombosis with or without pulmonary embolism when administered in conjunction with warfarin sodium. The sodium salt of tinazaparin is available under the trademark Innohep™ from Pharmion Corporation of Boulder, Colo. The term "very low molecular weight heparin" generally refers to heparin in which at least 80% (by weight) of the heparin has a molecular weight of between about 1500 and about 5000 daltons. Non-limiting examples of very low molecular weight heparin include bemiparin. The term "ultra low molecular weight heparin" generally refers to heparin in which at least 80% (by weight) of the heparin has a molecular weight of between about 1000 and about 2000 daltons. Non-limiting examples of ultra low molecular weight heparin include fondiparinux.

The term "insulin" refers to all forms of insulin, including, but not limited to, naturally derived insulin and synthetic forms of insulin, such as those described in U.S. Pat. Nos. 4,421,685, 5,474,978, and 5,534,488, each of which is hereby incorporated by reference in its entirety.

The term "AUC" as used herein, means area under the plasma concentration-time curve, as calculated by the trapezoidal rule over the complete dosing interval, e.g., 24-hour interval.

The term "mean", when preceding a pharmacokinetic value (e.g., mean Peak) represents the arithmetic mean value of the pharmacokinetic value unless otherwise specified.

As used herein, the term "about" means within 10% of a given value, preferably within 5%, and more preferably within 1% of a given value. Alternatively, the term "about" means that a value can fall within a scientifically acceptable error range for that type of value, which will depend on how qualitative a measurement can be given the available tools.

Anhydrous SNAC Form I

Figure 2:
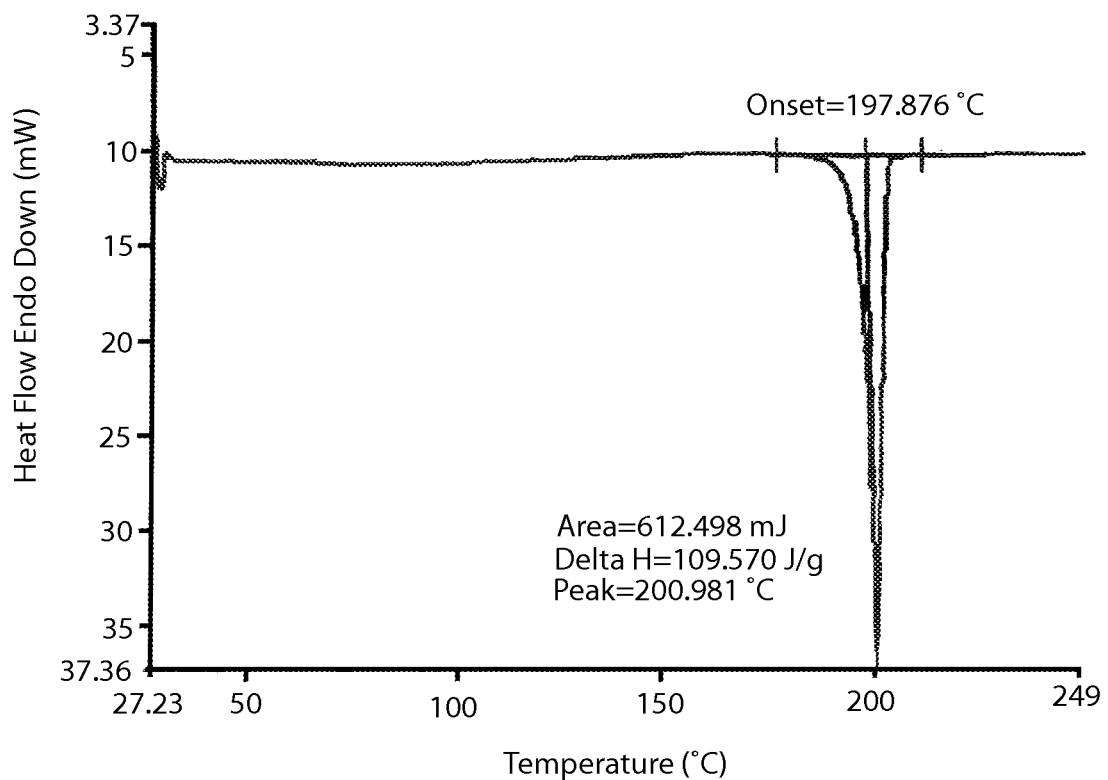
FIGS. 2, 7, 12, 17, 22, 27, and 44 are differential scanning calorimetry (DSC) analyses of Forms I-VI of SNAC and amorphous SNAC (containing approximately 10% Form III of SNAC), respectively, as prepared in Examples 1-6 and 14.
Figure 3:
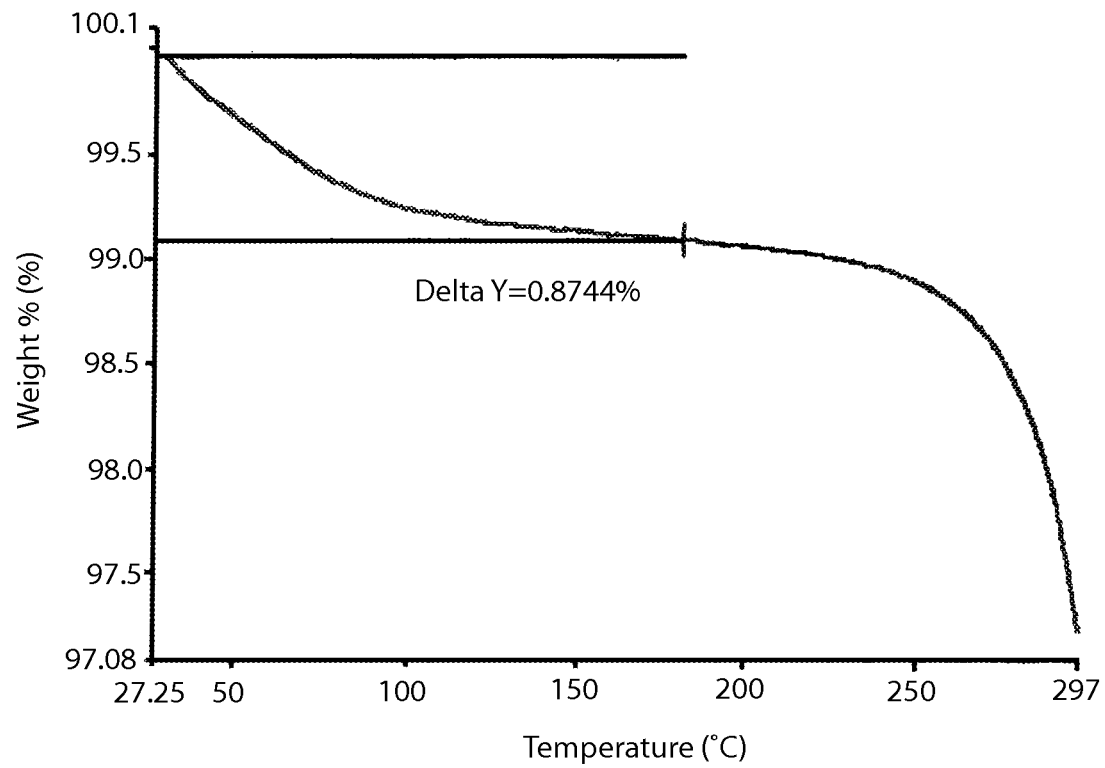
FIGS. 3, 8, 13, 18, 23, 28, and 45 are thermogravimetric analyses (TGAs) of Forms I-VI of SNAC and amorphous SNAC (containing approximately 10% Form III of SNAC), respectively, as prepared in Examples 1-6 and 14.
Figure 4:
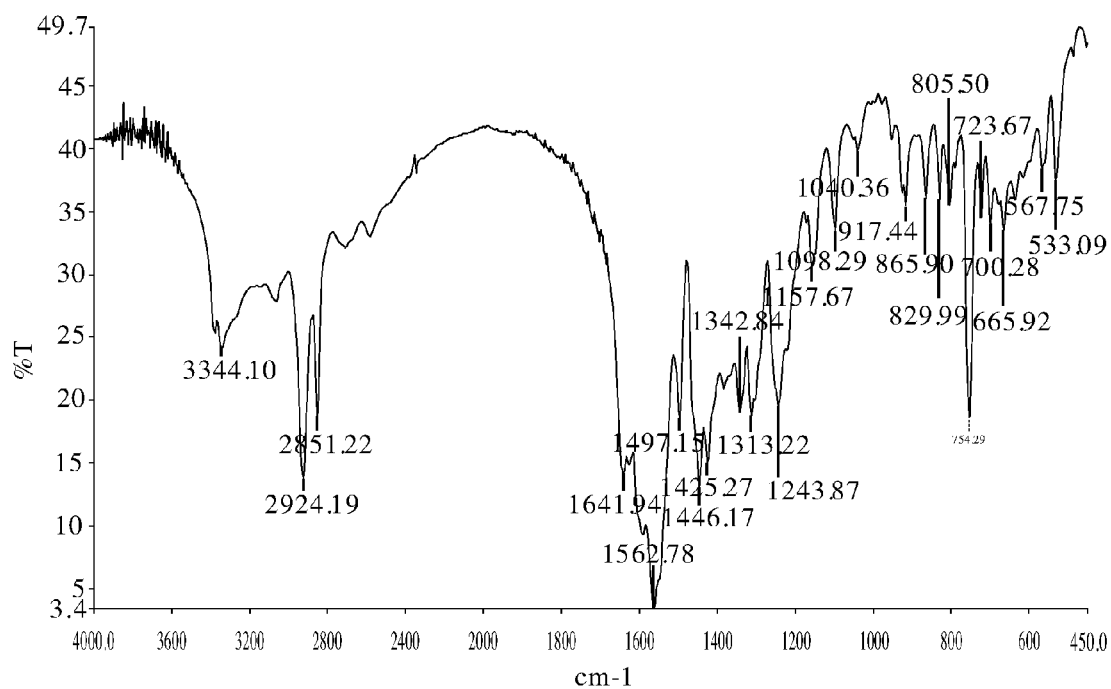
FIGS. 4, 9, 14, 19, 24, 29, and 46 are FTIR spectra of Forms I-VI of SNAC and amorphous SNAC (containing approximately 10% Form III of SNAC), respectively, as prepared in Examples 1-6 and 14.
Figure 5:
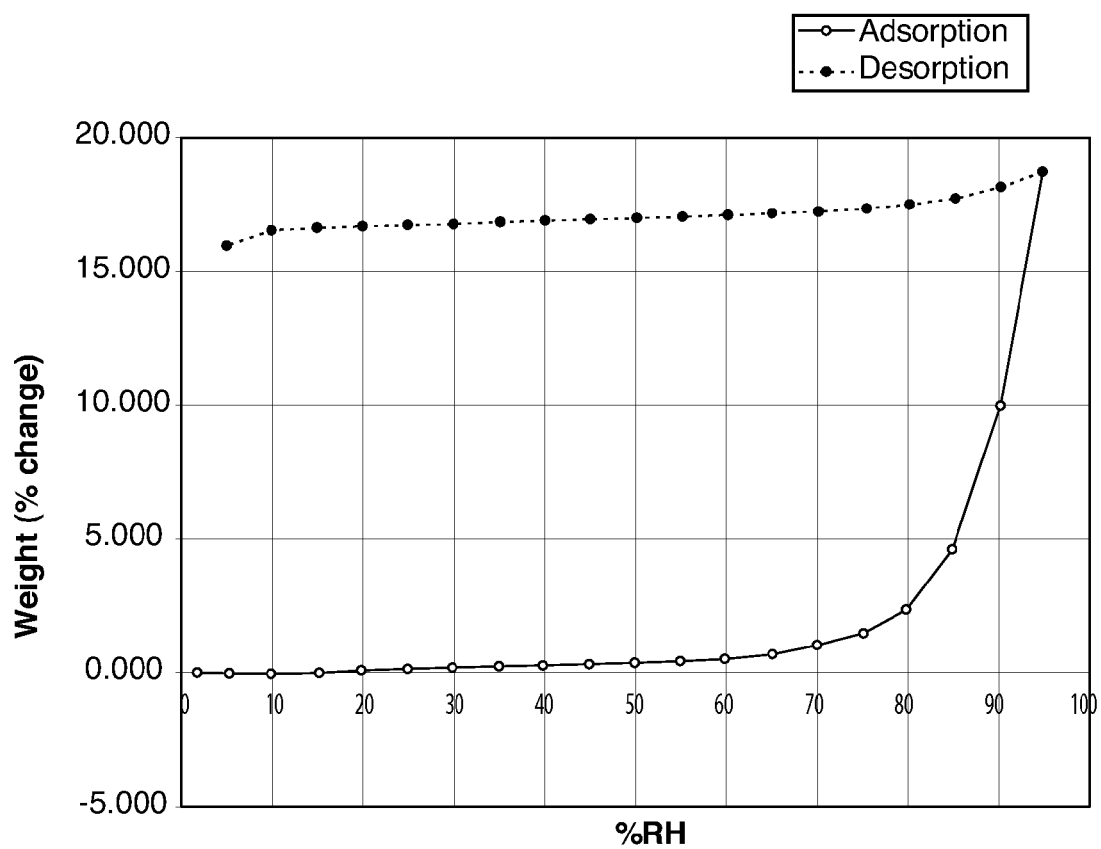
FIGS. 5, 10, 15, 20, 25, 30, and 47 are moisture adsorption/desorption spectra of Forms I-VI of SNAC and amorphous SNAC (containing approximately 10% Form III of SNAC), respectively, as prepared in Examples 1-6 and 14.

Crystalline polymorph Form I of SNAC is anhydrous. Form I is stable at room temperature, and does not change crystal form when subjected to milling (e.g., ball milling) or compression (e.g., direct compression). Form I, however, does convert to Form III when wet granulated with a sufficient amount of water for a sufficient amount of time. According to differential scanning calorimetry (DSC), Form I has a melting point onset at about 198° C. (see FIG. 2). Form I of SNAC has an XRPD pattern substantially identical to that shown in FIG. 1. Characteristic XRPD peak locations (expressed in degrees 2θ±0.2, 0.1, 0.05, or 0.01° 2θ) and d-spacing for Form I are provided in Table 1 below. The XRPD peak locations marked "(U)" in Table 1 are unique to Form I. For example, the peak at 2.98° 2θ±0.2, 0.1, 0.05, or 0.01° 2θ is unique to Form I.

TABLE 1

Characteristic XRPD Peaks (expressed in degrees 2θ) of Form I of SNAC

| Degrees 2θ ± 0.2° 2θ | d (Å) |
|---|---|
| 2.98 (U) | 29.59 |
| 5.85 | 15.09 |
| 8.66 | 10.20 |
| 11.56 | 7.65 |
| 14.53 (U) | 6.09 |
| 15.72 (U) | 5.63 |
| 18.88 | 4.69 |
| 22.12 | 4.02 |
| 26.36 (U) | 3.38 |
| 30.88 | 2.89 |

Form I may be prepared by the procedure described in Example 1 below.

Form I may also be prepared by heating Form III, V, or VI or a mixture thereof to a temperature of at least 50° C. (but preferably less than 110° C.).

Form I may further be prepared by heating amorphous SNAC at from about 30 to about 90° C., and preferably from about 40 to about 80° C., for a time sufficient to form Form I of SNAC.

Another method of preparing Form I is by lyophilizing any form of SNAC other than Form I to yield Form I. For example, one or more of Forms II-VI of SNAC and/or amorphous SNAC can be lyophilized to yield Form I.

The present invention also provides a pharmaceutical composition containing Form I of SNAC in which less than 90, 80, 70, or 60% of the SNAC is crystalline (based on 100% total weight of SNAC).

The present invention also provides a pharmaceutical composition, such as a tablet, comprising a milled (e.g., ball milled) or directly compressed mixture of Form I of SNAC and at least one active agent and/or pharmaceutically acceptable additive (such as those described below). Preferably, the pharmaceutical composition (or milled or directly compressed mixture) includes at least 50, 60, 70, 80, 90, 95, 96, 97, 98, or 99% by weight of Form I based on the total weight of SNAC in the pharmaceutical composition (or milled or directly compressed mixture).

SNAC Hydrate Form II

Figure 6:
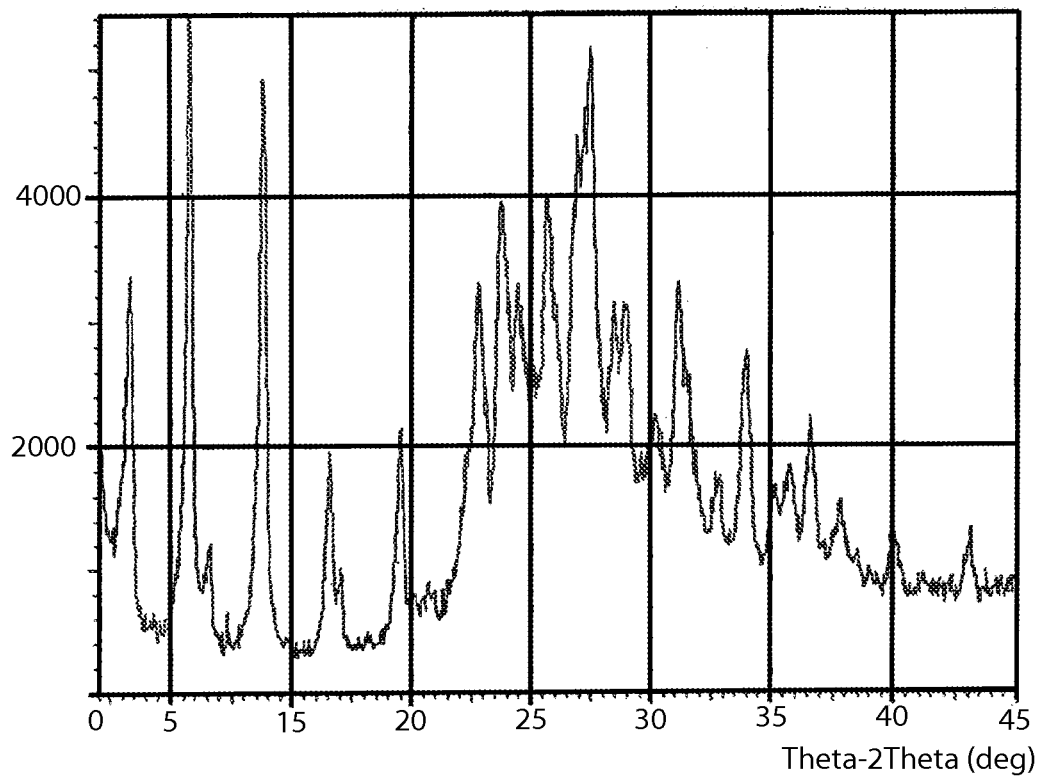
Figure 7:
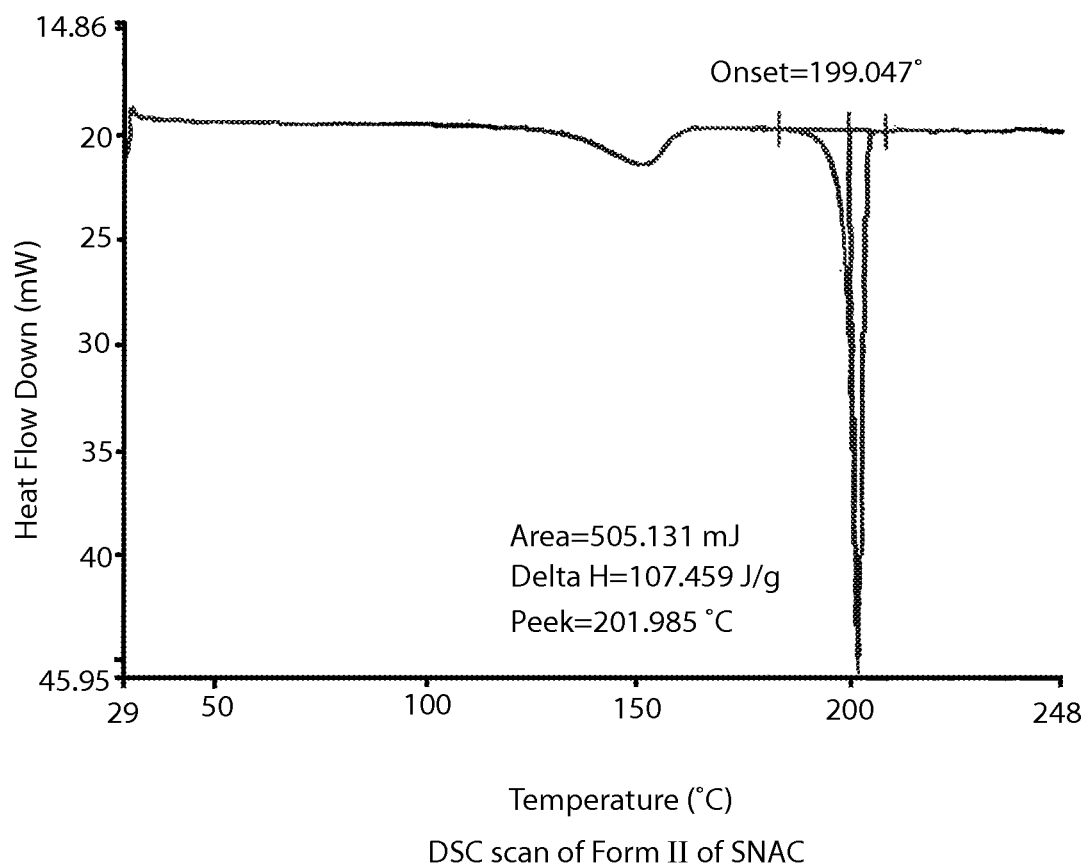
Figure 8:
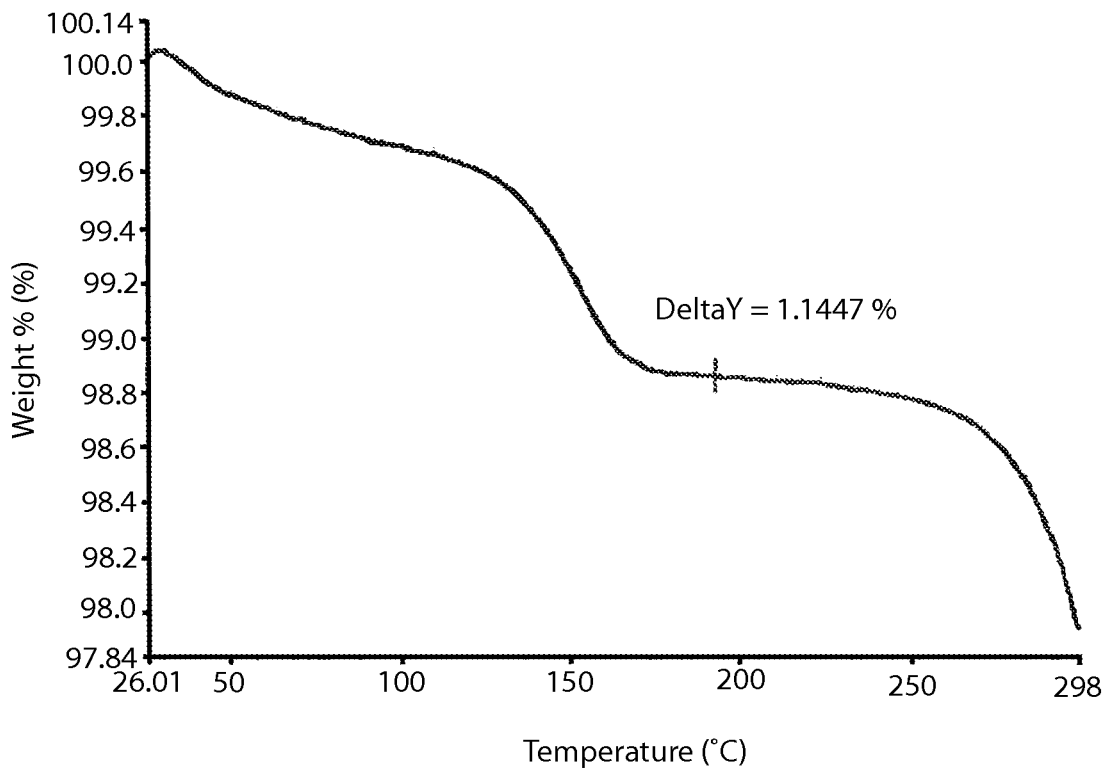
Figure 9:
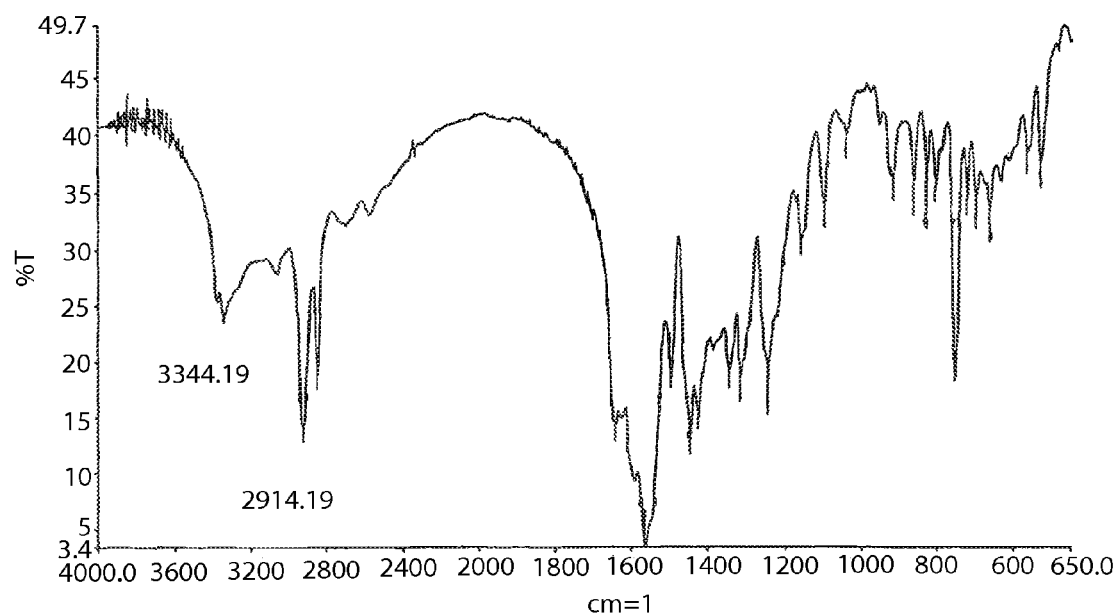
Figure 10:
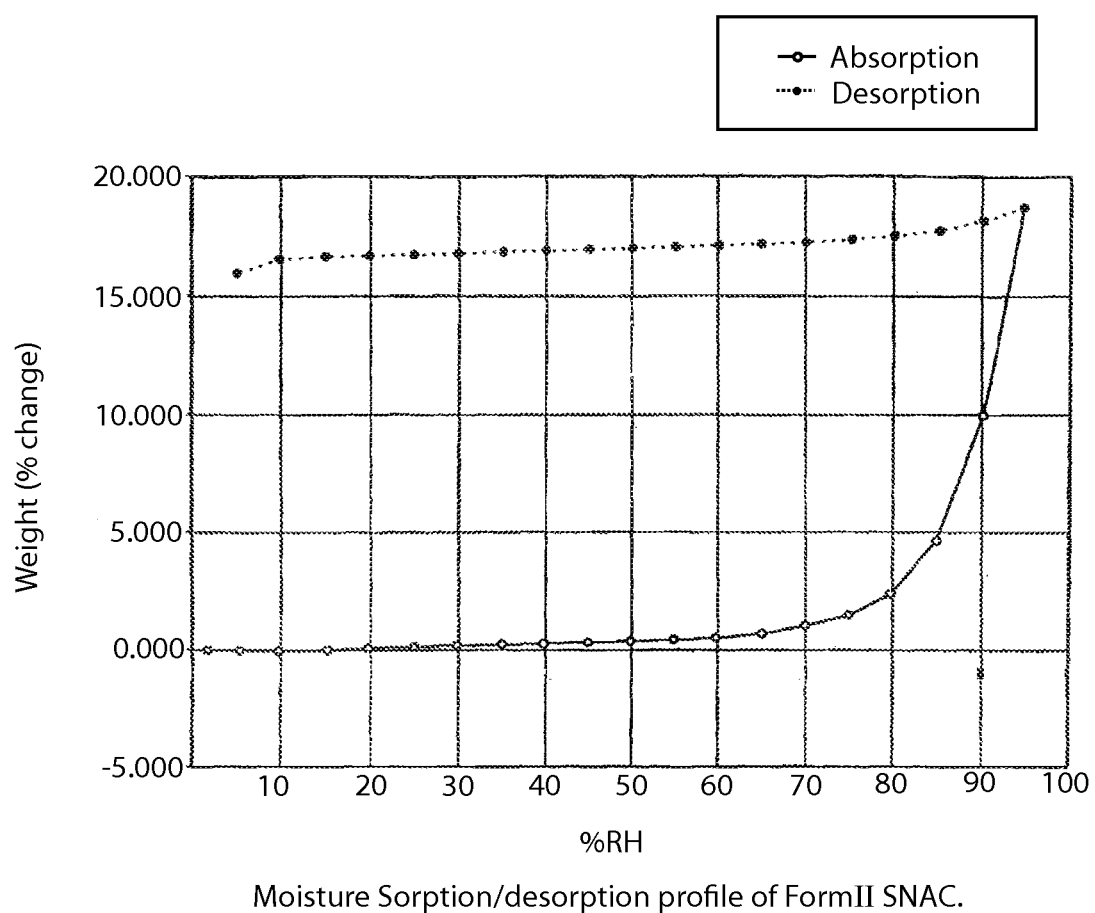

Crystalline polymorph Form II is a hydrate of SNAC. Without being bound by any particular theory, the inventor theorizes that Form II is a 1/3 hydrate (i.e., it has approximately 1 mole of water per 3 moles of SNAC (also referred to as SNAC 1/3 hydrate)). Form II is stable at room temperature. According to DSC, Form II has a melting point onset at about 199° C. (see FIG. 7). Form II of SNAC has an XRPD pattern substantially identical to that shown in FIG. 6. Characteristic XRPD peak locations (expressed in degrees 2θ±0.2, 0.1, 0.05, or 0.01° 2θ) and d-spacing for Form II are provided in Table 2 below. The XRPD peak locations marked "(U)" in Table 2 are unique to Form II. For example, the peaks at 3.29, 11.96, and 17.76° 2θ±0.2, 0.1, 0.05, or 0.01° 2θ are unique to Form II.

TABLE 2

Characteristic XRPD Peaks (expressed in degrees 2θ) of Form II of SNAC

| Degrees 2θ ± 0.2° 2θ | d (Å) |
|---|---|
| 3.29 (U) | 26.83 |
| 5.78 (U) | 15.27 |
| 6.56 (U) | 13.46 |
| 8.76 | 10.08 |
| 11.53 | 7.67 |
| 11.96 (U) | 7.39 |
| 14.47 (U) | 6.11 |
| 17.12 (U) | 5.17 |
| 17.76 (U) | 4.99 |
| 18.08 (U) | 4.90 |
| 18.76 (U) | 4.72 |
| 19.44 | 4.56 |
| 20.16 | 4.40 |
| 20.72 (U) | 4.28 |
| 21.12 (U) | 4.20 |
| 21.84 | 4.07 |
| 22.48 | 3.95 |
| 23.44 (U) | 3.79 |
| 23.96 (U) | 3.71 |
| 24.56 (U) | 3.62 |
| 25.16 (U) | 3.54 |
| 25.40 (U) | 3.50 |
| 26.20 (U) | 3.40 |
| 26.48 (U) | 3.36 |
| 26.88 (U) | 3.31 |
| 27.73 (U) | 3.21 |
| 28.95 | 3.08 |
| 30.12 (U) | 2.96 |
| 30.69 (U) | 2.91 |
| 31.57 (U) | 2.83 |
| 32.76 (U) | 2.73 |
| 34.99 (U) | 2.56 |
| 37.98 (U) | 2.37 |

Form II of SNAC may be prepared by drying (e.g., tumble drying) a solvate (e.g., an ethanol solvate or methanol solvate) of SNAC without agitation and exposing the dried SNAC to moisture for a sufficient time to yield Form II of SNAC. Preferably, the drying and exposure steps are performed in a closed container. The exposure step may be performed subsequent to the drying step. The dried SNAC may optionally be stored in a moist environment (e.g., at ambient conditions or in a humid environment (e.g., a relative humidity of 10 or 20% or more)) to cause conversion of any remaining SNAC, which is not Form II SNAC, to Form II. An ethanol solvate of SNAC may be prepared by the procedure described in Example 2.

SNAC Hydrate Form III

Figure 11:
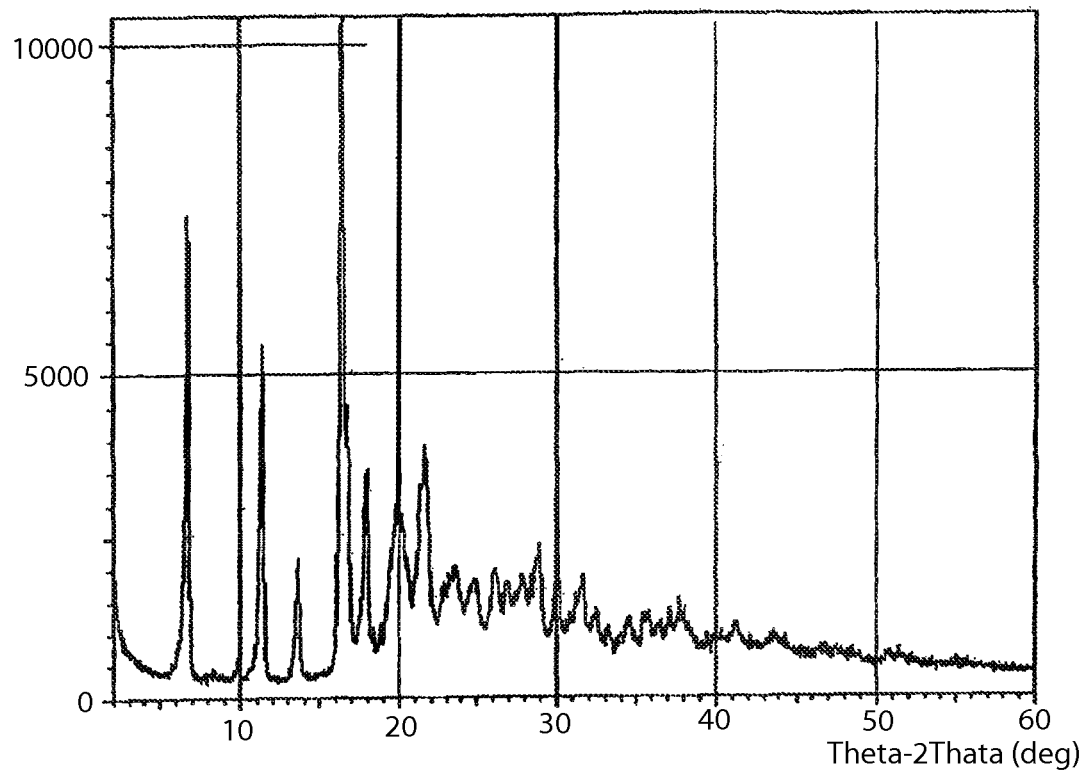
Figure 12:
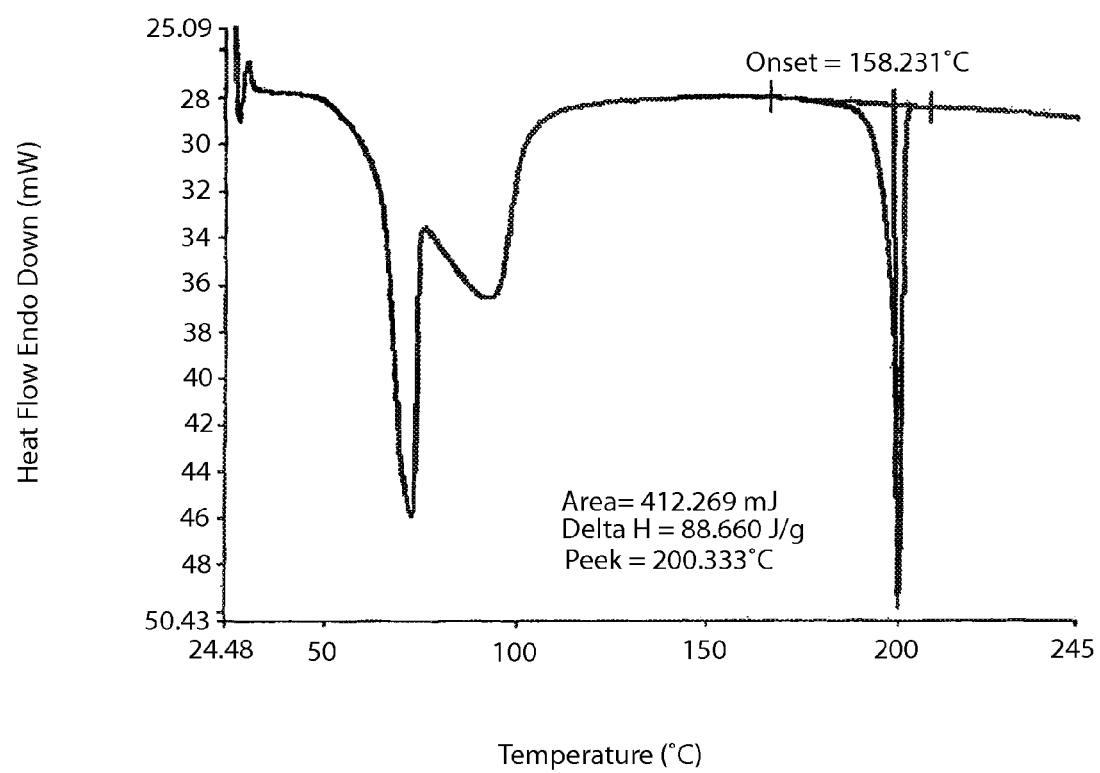
Figure 13:
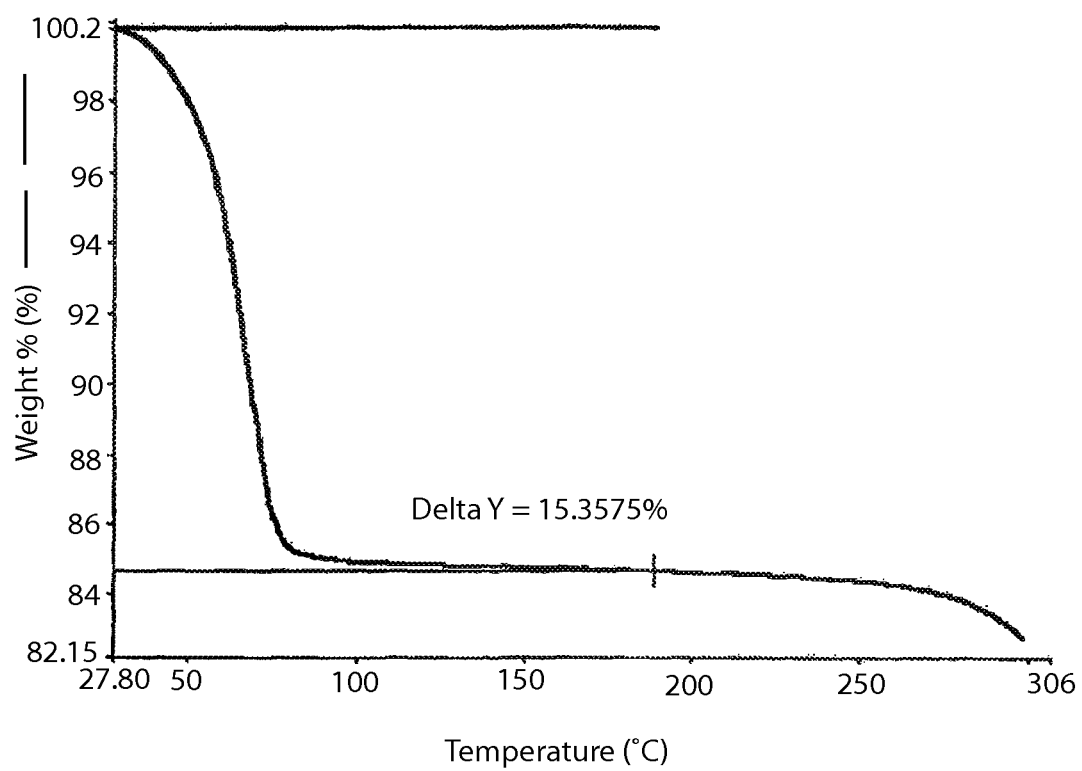
Figure 14:
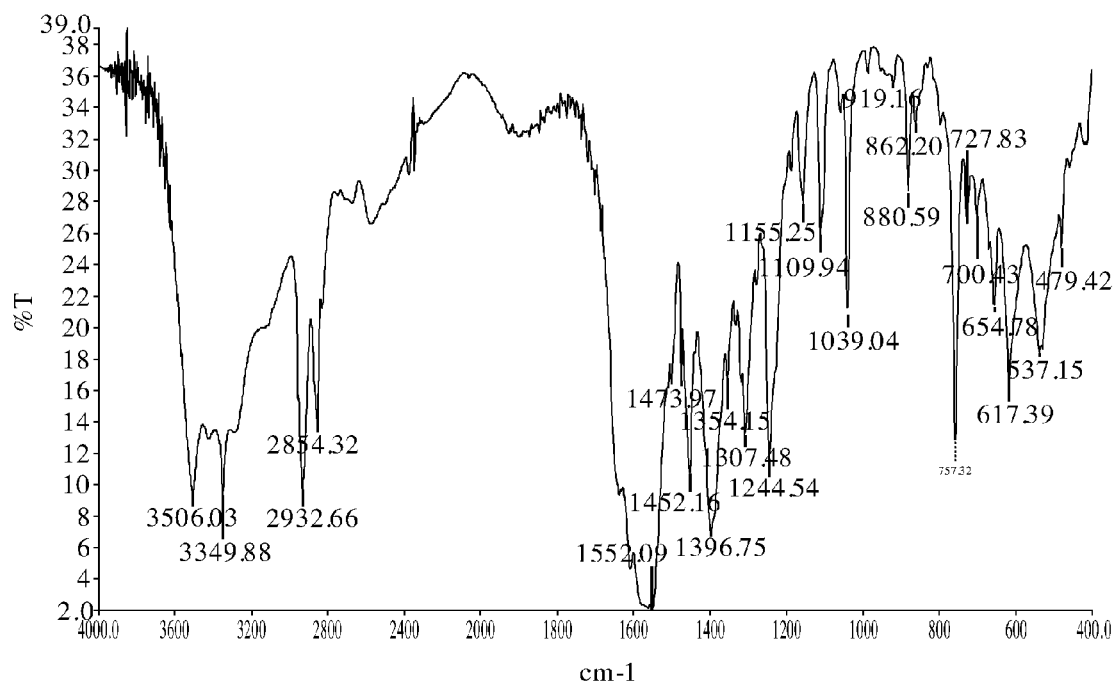
Figure 15:
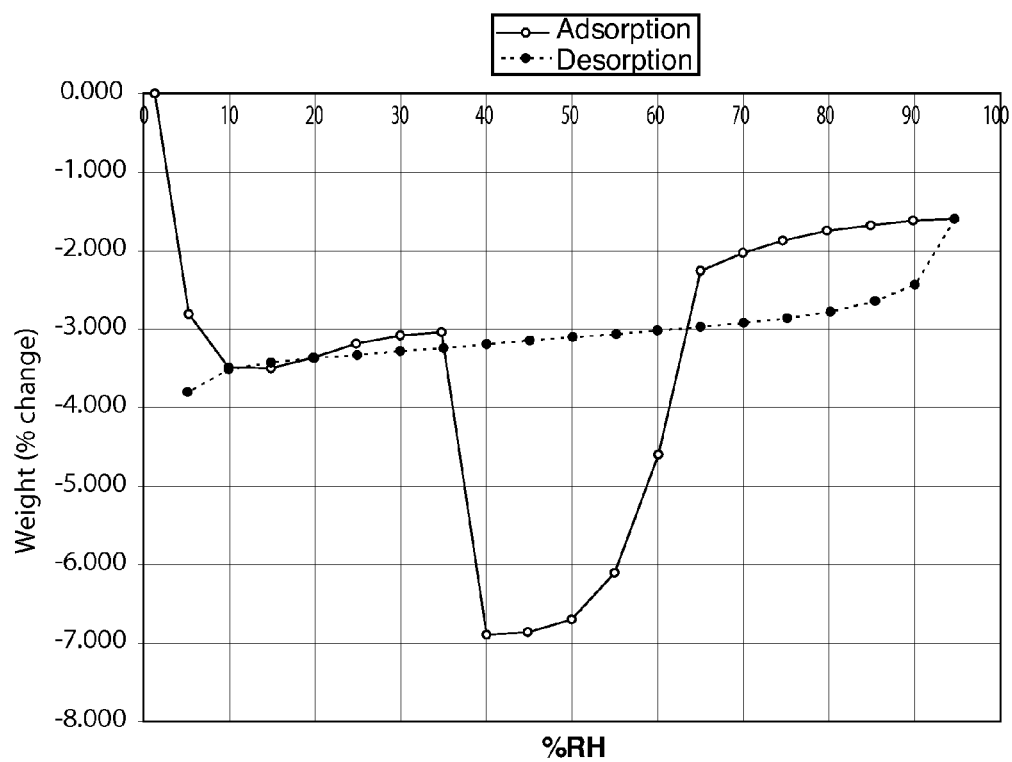

Crystalline polymorph Form III is a hydrate of SNAC. Without being bound by any particular theory, the inventor theorizes that Form III is a trihydrate (i.e., it has approximately 3 moles of water per mole of SNAC (also referred to as SNAC trihydrate)). Form III is stable at room temperature, and does not change crystal form when subjected to compression (e.g., direct compression). According to differential scanning calorimetry (DSC), Form III has a melting point onset at about 198° C. (see FIG. 12). Form III of SNAC has an XRPD pattern substantially identical to that shown in FIG. 11. Characteristic XRPD peak locations (expressed in degrees 2θ±0.2, 0.1, 0.05, or 0.01° 2θ) and d-spacing for Form III are provided in Table 3 below. The XRPD peak locations marked "(U)" in Table 3 are unique to Form III. For example, the peaks at 6.69, 13.58, and 16.80° 2θ±0.2, 0.1, 0.05, or 0.01° 2θ are unique to Form III.

TABLE 3

Characteristic XRPD Peaks (expressed in degrees 2θ) of Form III of SNAC

| Degrees 2θ ± 0.2° 2θ | d (Å) |
|---|---|
| 6.69 (U) | 13.20 |
| 11.31 (U) | 7.78 |
| 13.58 (U) | 6.51 |
| 16.41 (U) | 5.40 |
| 16.80 (U) | 5.27 |
| 17.91 (U) | 4.95 |
| 19.40 | 4.57 |
| 19.92 (U) | 4.45 |
| 20.16 | 4.40 |
| 20.56 (U) | 4.32 |
| 21.32 (U) | 4.16 |
| 21.60 (U) | 4.11 |
| 23.56 (U) | 3.77 |
| 24.84 (U) | 3.58 |
| 26.13 | 3.41 |
| 28.80 | 3.10 |
| 30.01 (U) | 2.97 |

Form III may be prepared by exposing Form I, II, IV, V, or VI or a mixture thereof to an environment having a relative humidity of 75%, 85%, 90%, or greater, for a sufficient time (e.g., seven days or longer) to yield Form III. For example, Form III can be prepared by exposing any of Forms I, II, or IV-VI to an environment having a relative humidity of 75% or greater for at least seven days (e.g., until the moisture content of the material is at least about 15% w/w). If the moisture content of the material is significantly greater than 15% w/w, the material is preferably dried at ambient conditions until the material has a moisture content of about 15% w/w.

Form III may also be prepared by exposing amorphous SNAC to moisture (i.e., an environment having a relative humidity greater than 0% and preferably greater than 5 or 10%) for a sufficient time to yield Form III.

Form III may also be prepared by wet granulation (aqueous granulation) of Form I, II, IV, V, or IV of SNAC or amorphous SNAC or a mixture thereof. According to one embodiment, Form I is wet granulated. The Form III produced may subsequently directed (e.g., at 50° C.) to obtain Form I of SNAC again.

Yet another method of preparing Form III is by exposing Form V or VI of SNAC or a mixture thereof to an environment having a relative humidity of 30%, 35%, 40%, 50%, or greater, for a sufficient time to yield Form III. Another method of preparing Form III is by exposing Form VI of SNAC or a mixture thereof to an environment having a relative humidity of 10%, 20%, 30%, or greater, for a sufficient time to yield Form III.

Form III may also be prepared by crystallizing SNAC from water. Crystals formed may be isolated by, for example, filtering and drying at ambient conditions. Preferably, drying is performed at less than 40 or 35° C.

The present invention also provides a pharmaceutical composition, such as a tablet, comprising a directly compressed mixture of Form III of SNAC and at least one active agent and/or pharmaceutically acceptable additive (such as those described below). Preferably, the pharmaceutical composition (or directly compressed mixture) includes at least 50, 60, 70, 80, 90, 95, 96, 97, 98, or 99% by weight of Form III based on the total weight of SNAC in the pharmaceutical composition (or directly compressed mixture).

Anhydrous SNAC Form IV

Figure 16:
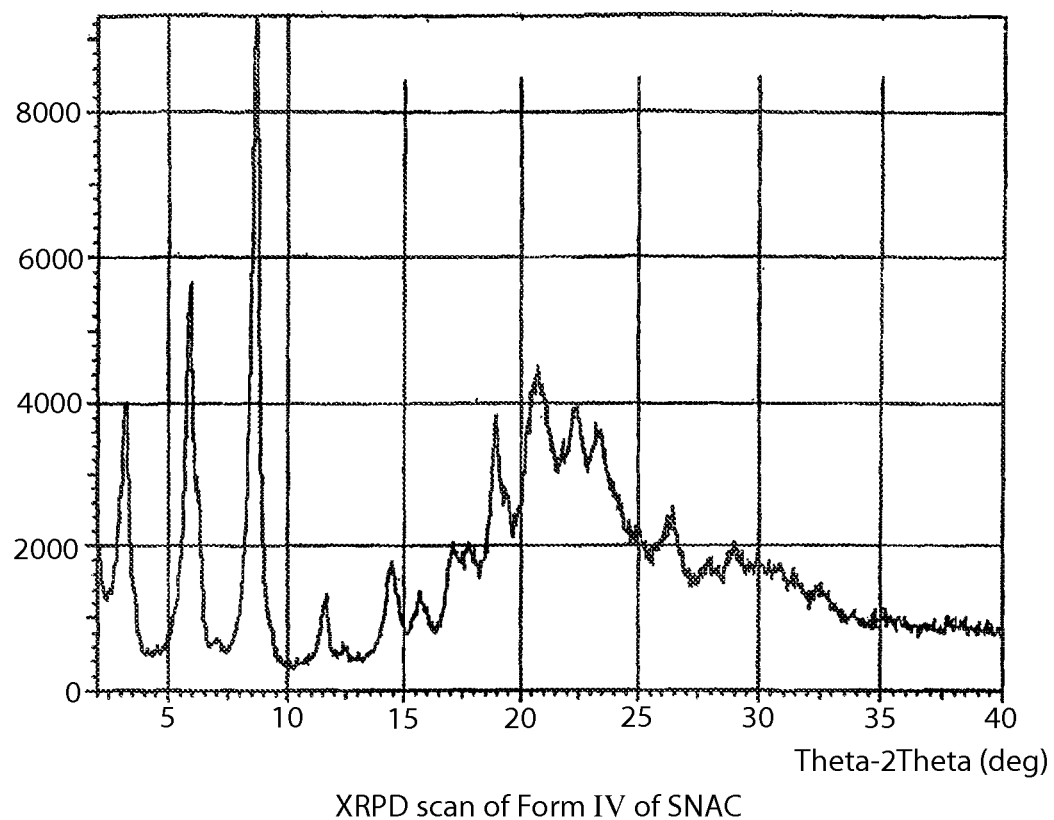
Figure 17:
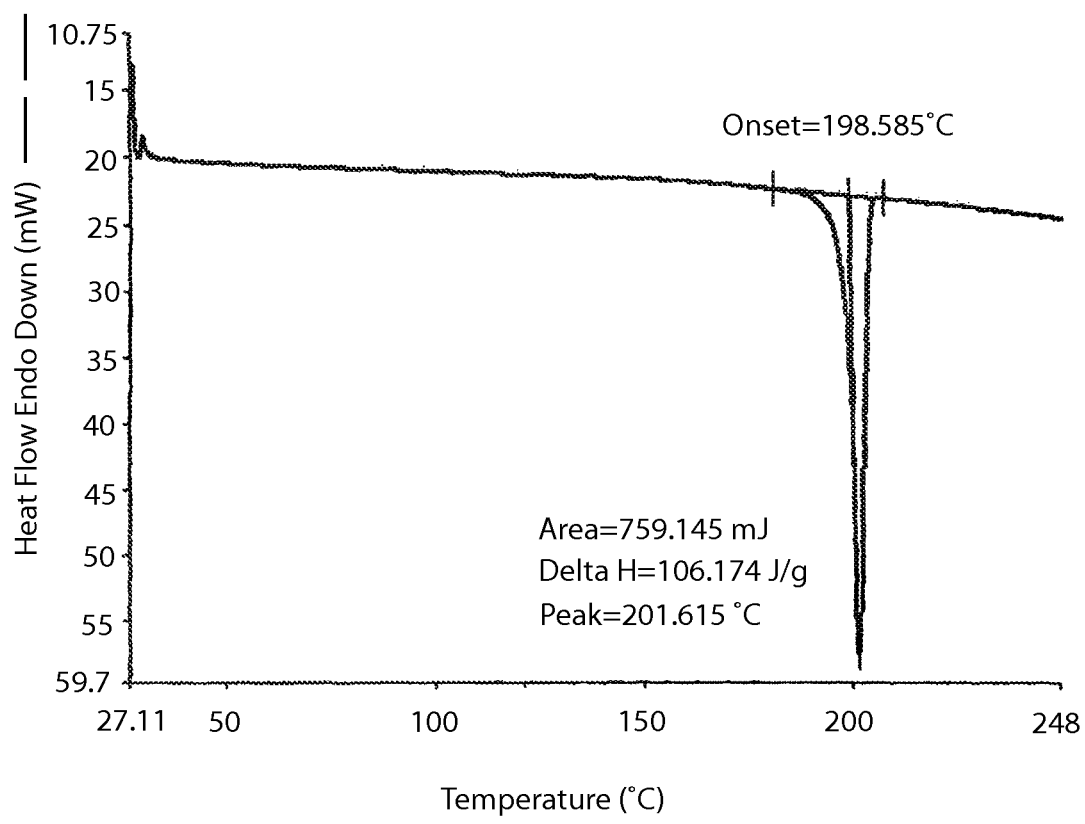
Figure 18:
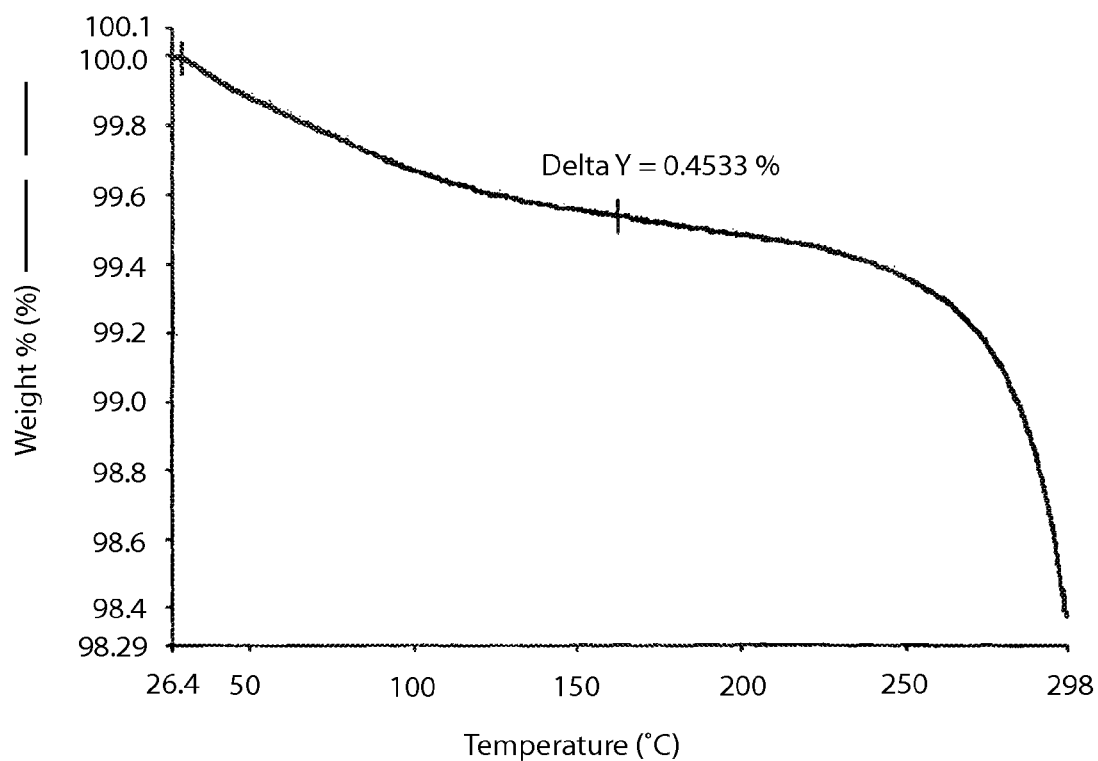
Figure 19:
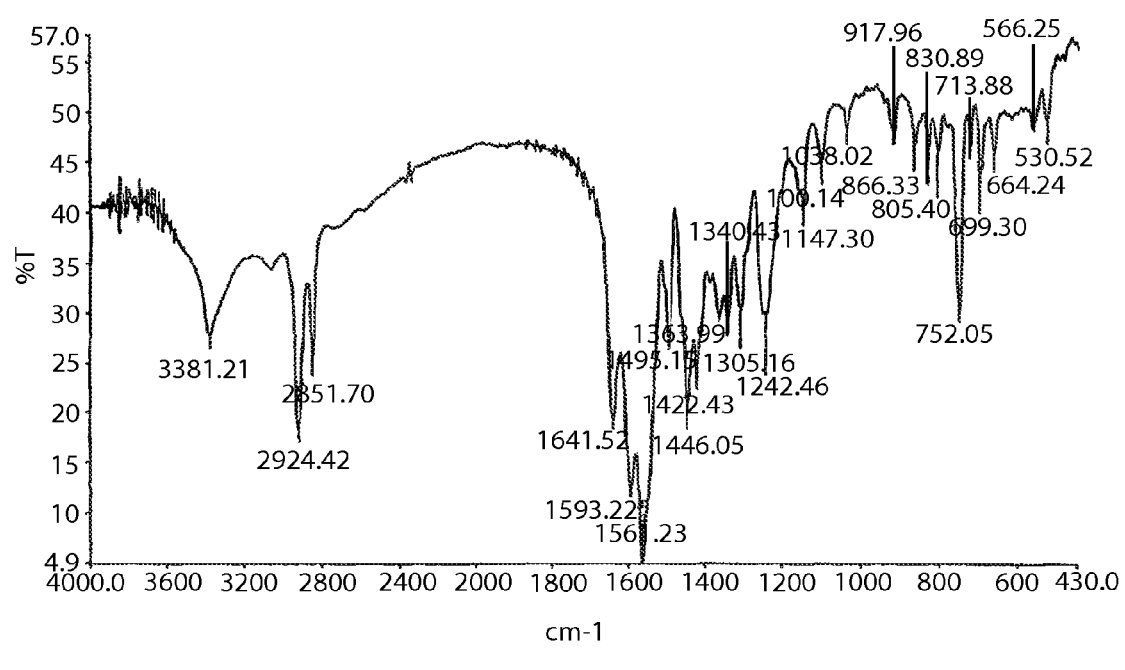
Figure 20:
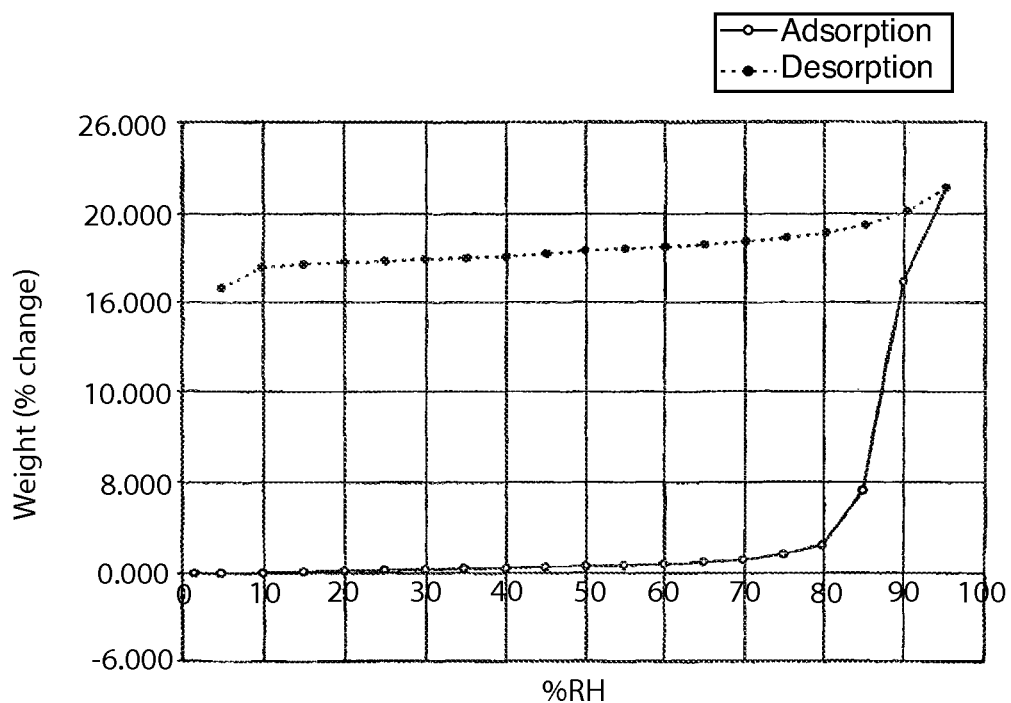

Crystalline polymorph Form IV of SNAC is anhydrous. Form IV is stable at room temperature. Furthermore, Form IV is less soluble in acetonitrile and more thermodynamically stable than Form I at ambient conditions. According to differential scanning calorimetry (DSC), Form IV has a melting point onset at about 199° C. (see FIG. 17). Form IV of SNAC has an XRPD pattern substantially identical to that shown in FIG. 16. Characteristic XRPD peak locations (expressed in degrees 2θ±0.2, 0.1, 0.05, or 0.01° 2θ) and d-spacing for Form IV are provided in Table 4 below. The XRPD peak locations marked "(U)" in Table 4 are unique to Form IV. For example, the peaks at 8.61, 17.04, and 23.28° 2θ±0.2, 0.1, 0.05, or 0.01° 2θ are unique to Form IV.

TABLE 4

Characteristic XRPD Peaks (expressed in degrees 2θ) of Form IV of SNAC

| Degrees 2θ ± 0.2° 2θ | d (Å) |
|---|---|
| 3.16 U | 27.91 |
| 5.89 | 14.98 |
| 6.32 U | 13.97 |
| 8.61 U | 10.26 |
| 11.55 U | 7.65 |
| 14.45 U | 6.13 |
| 17.04 U | 5.20 |
| 18.92 | 4.68 |
| 20.80 | 4.27 |
| 21.16 | 4.19 |
| 22.36 U | 3.97 |
| 23.28 U | 3.82 |
| 23.76 U | 3.74 |

Form IV may be prepared by heating Form I, II, III, V or VI of SNAC or a mixture thereof to a temperature between about 110 or 150° C. and the melting point of SNAC for a sufficient time to yield Form IV. For example, Form II of SNAC may be heated (such as in a dry oven) to a temperature greater than the transition temperature of the desolvated material but lower than the melting temperature of SNAC (e.g., dehydration occurs at a heating rate of 10° C./min with onset at about 130-140° C.) until Form IV is formed (e.g., for several hours). After formation, Form IV can be cooled and recovered.

The present invention also provides a pharmaceutical composition containing Form IV of SNAC in which at least 50, 60, 70, 80 or 90% of the SNAC is crystalline (based on 100% weight of SNAC).

Methanol-Water Co-Solvate of SNAC Form V

Figure 21:
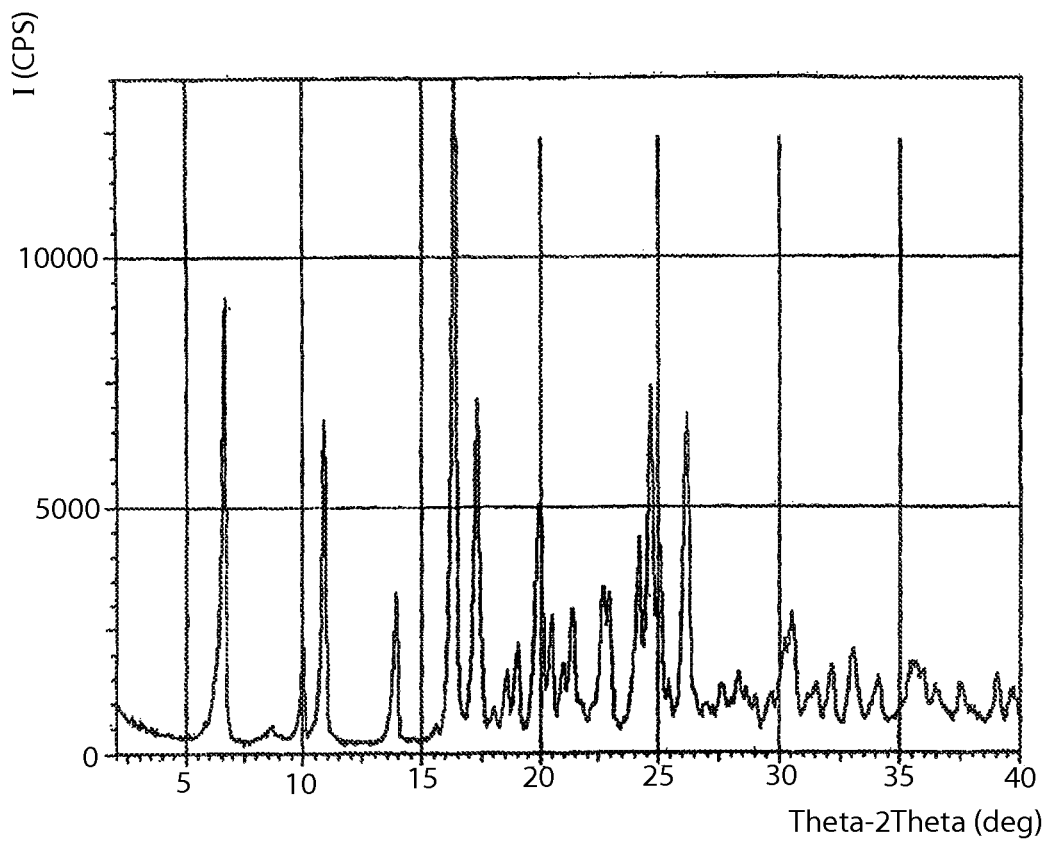
Figure 22:
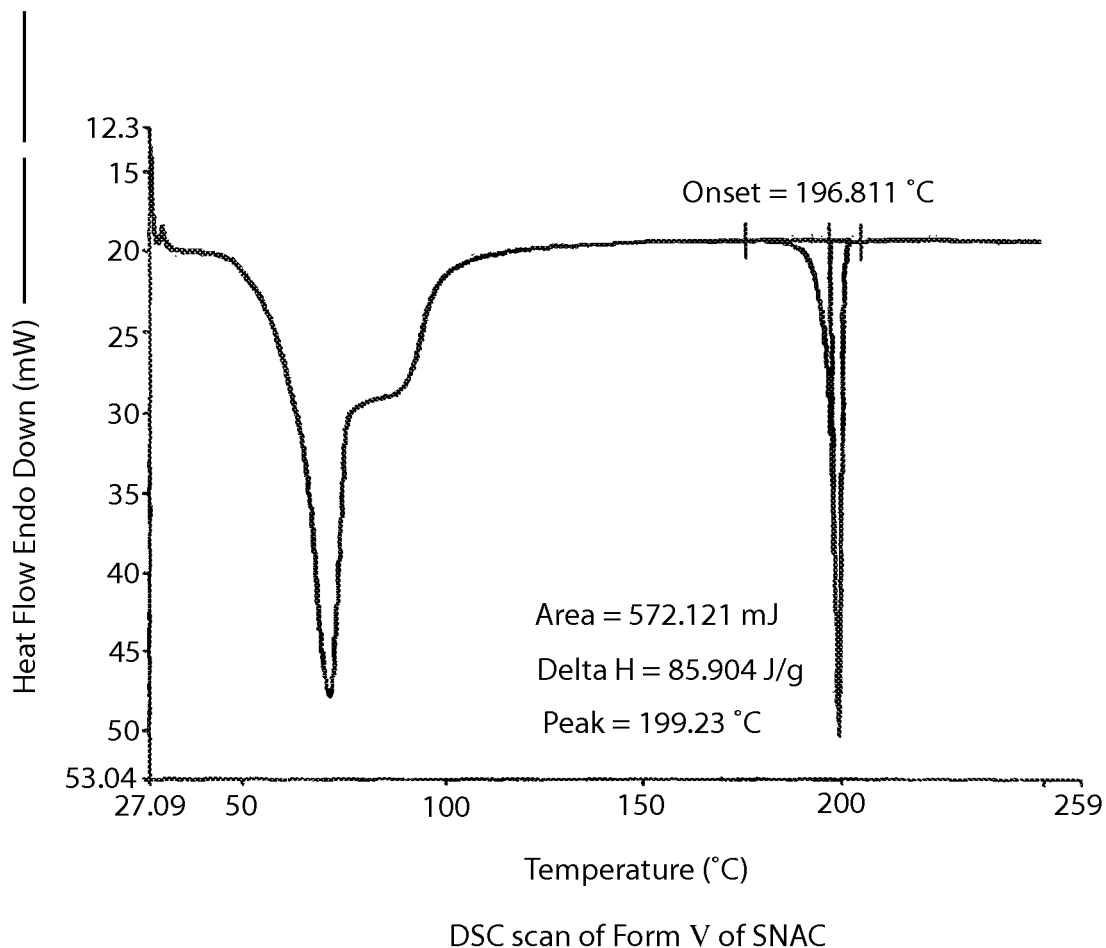
Figure 23:
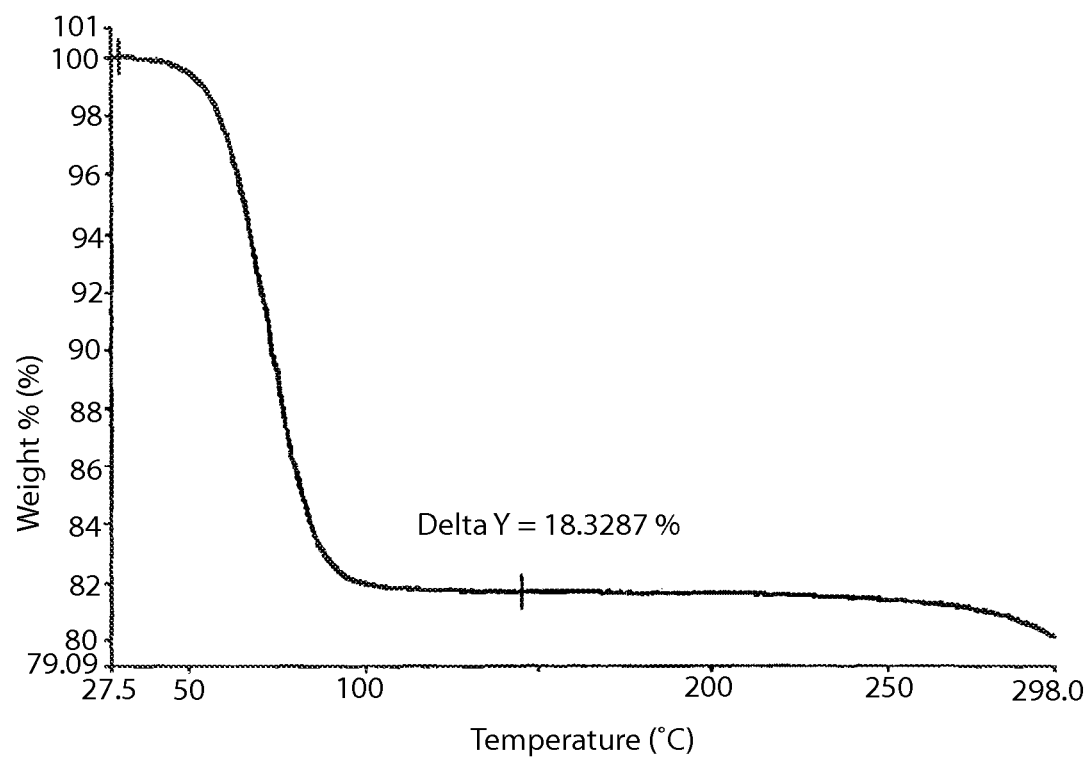
Figure 24:
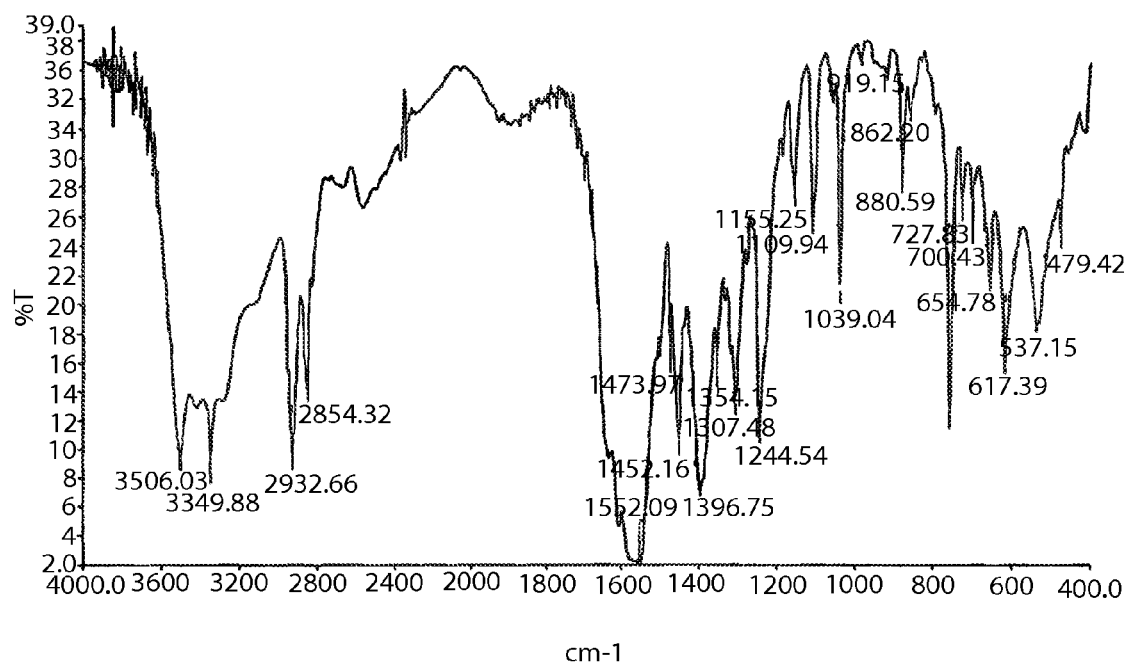
Figure 25:
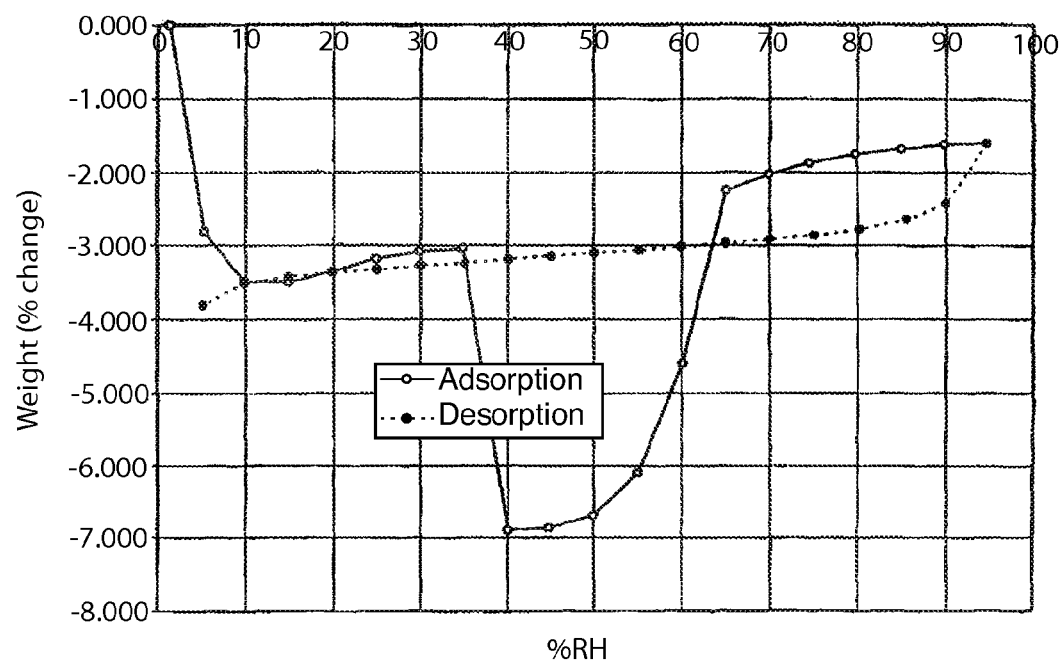

Crystalline polymorph Form V of SNAC is a methanol-water co-solvate (approximately 0.8 moles of methanol and 2 moles of water per 1 mole of SNAC). According to differential scanning calorimetry (DSC), Form V has a melting point onset at about 197° C. (see FIG. 22). Form V of SNAC has an XRPD pattern substantially identical to that shown in FIG. 21. Characteristic XRPD peak locations (expressed in degrees 2θ±0.2, 0.1, 0.05, or 0.01° 2θ) and d-spacing for Form V are provided in Table 5 below. The XRPD peak locations marked "(U)" in Table 5 are unique to Form V. For example, the peaks at 6.59, 9.96, 10.86, 13.87, 17.29, and 19.92° 2θ±0.2, 0.1, 0.05, or 0.01° 2θ are unique to Form V.

TABLE 5

Characteristic XRPD Peaks (expressed in degrees 2θ) of Form V of SNAC

| Degrees 2θ ± 0.2° 2θ | d (Å) |
|---|---|
| 6.24 U | 14.15 |
| 6.59 U | 13.39 |
| 9.96 U | 8.87 |
| 10.86 U | 8.14 |
| 13.87 U | 6.38 |
| 16.35 | 5.42 |
| 17.29 U | 5.12 |
| 18.99 U | 4.67 |
| 19.92 U | 4.45 |
| 20.44 U | 4.34 |
| 21.35 U | 4.16 |
| 22.68 U | 3.92 |
| 22.92 U | 3.88 |
| 24.16 U | 3.68 |
| 24.64 U | 3.61 |
| 25.04 U | 3.55 |
| 26.13 | 3.41 |
| 30.20 U | 2.96 |
| 30.48 U | 2.93 |
| 31.52 U | 2.84 |
| 32.13 U | 2.78 |
| 33.03 U | 2.71 |
| 34.04 U | 2.63 |
| 35.44 U | 2.53 |
| 35.64 U | 2.52 |
| 35.92 U | 2.50 |
| 36.49 U | 2.46 |
| 37.50 U | 2.40 |
| 39.03 U | 2.31 |

Form V may be prepared by crystallization of SNAC (e.g., Form I-IV or VI of SNAC or a mixture thereof (e.g., a mixture of Forms I and III)) from a methanol solution at a relative humidity of at least about 30, 40, or 50%. Preferably, the methanol solution is substantially free or completely free of water. For example, Form V may be prepared by preparing a saturated solution of SNAC (e.g., Form I-IV or VI of SNAC or a mixture thereof) in methanol at a relative humidity of at least about 30, 40, or 50%, and cooling the solution, e.g., to room temperature or lower (such as in an ice bath). The resulting precipitate can be filtered and dried.

Form V may also be prepared by equilibration of Forms I-IV or VI of SNAC with methanol. Preferably, the methanol is substantially or completely free of water. For example, Form V can be prepared by slurring any of Forms I-IV or VI or a mixture thereof in methanol at a relative humidity of at least 30, 40, or 50% (e.g., to cause precipitation of the SNAC out of solution), and maintaining the slurried mixture at ambient temperatures for a sufficient time to form Form V (e.g., several days). Preferably, an excess of methanol (i.e., the molar ratio of methanol to SNAC is greater than 1) is used. The resulting solid may be recovered, e.g., by vacuum filtration and air-drying.

Ethanol-Water Co-Solvate of SNAC Form VI

Figure 26:
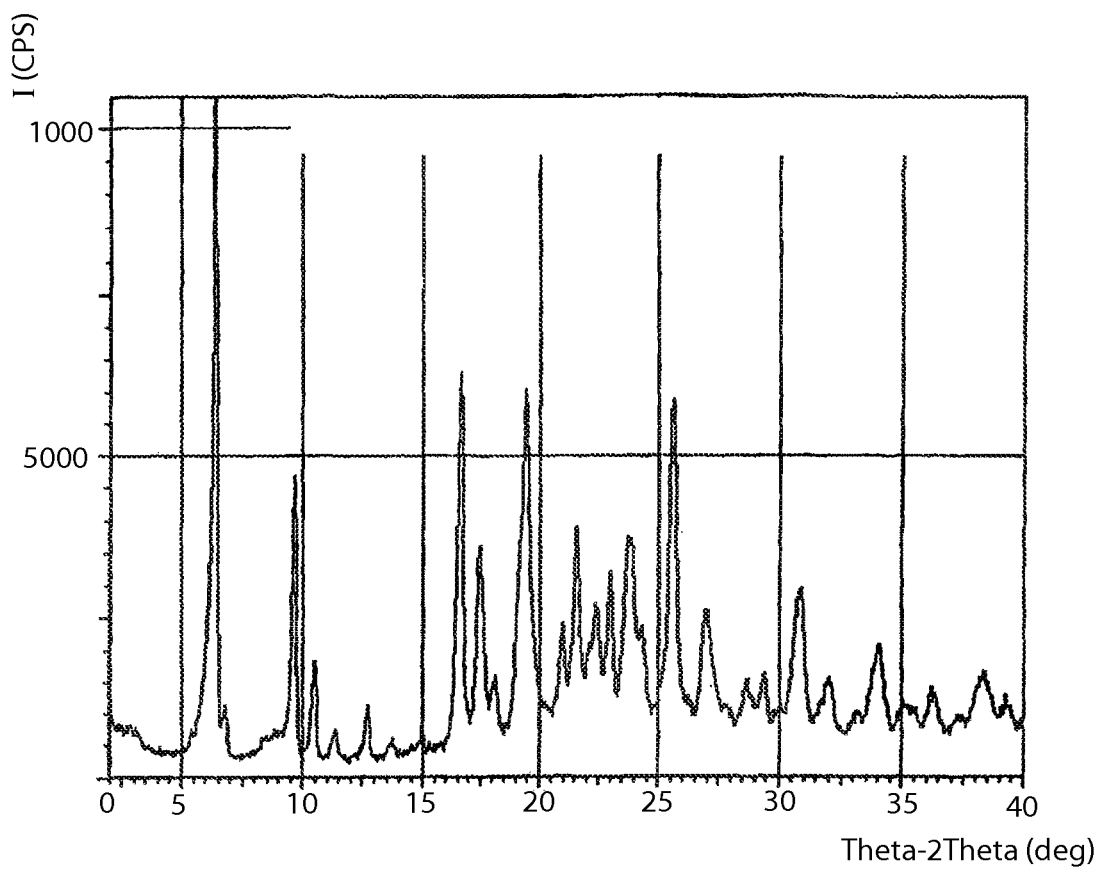
Figure 27:
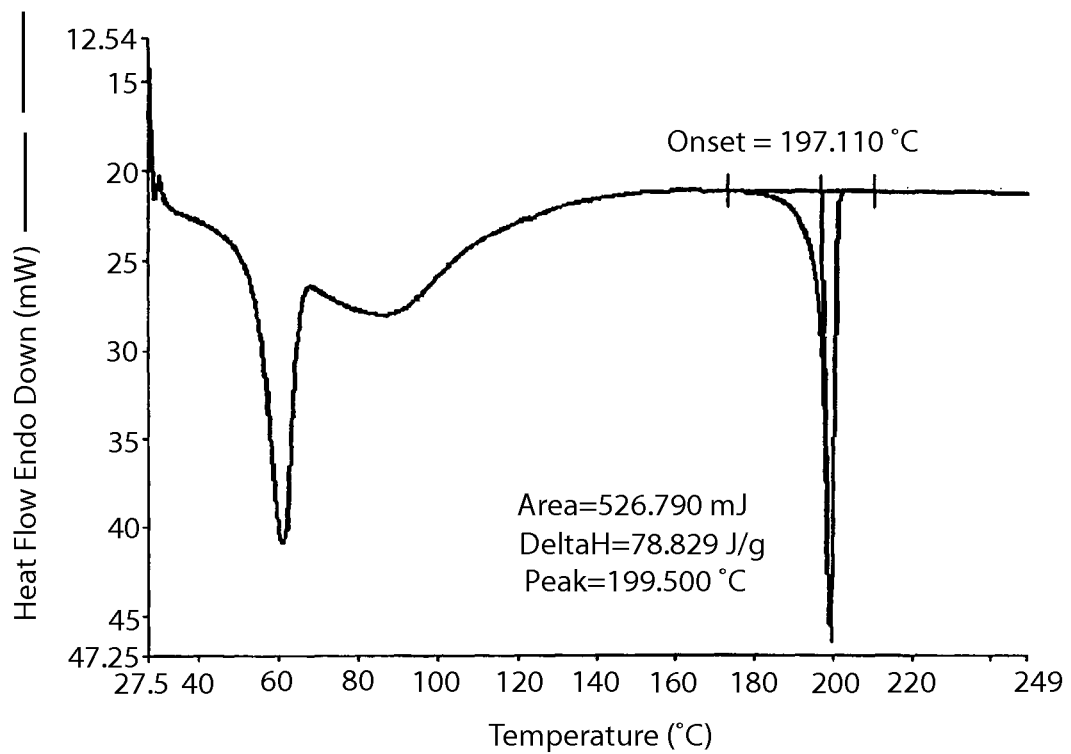
Figure 28:
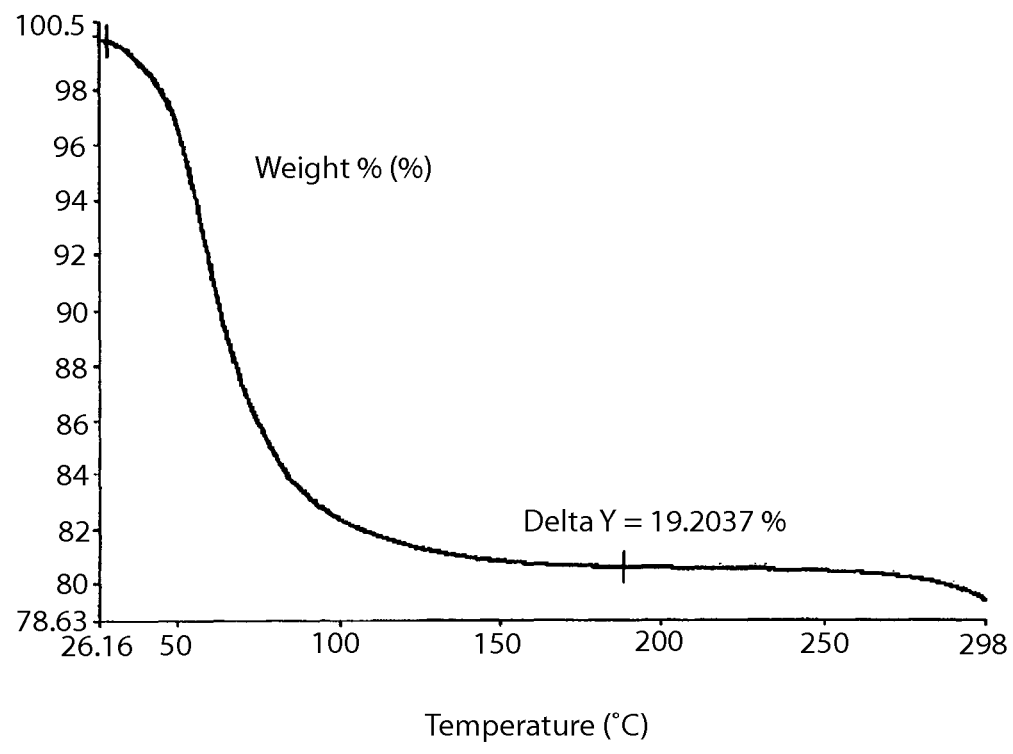
Figure 29:
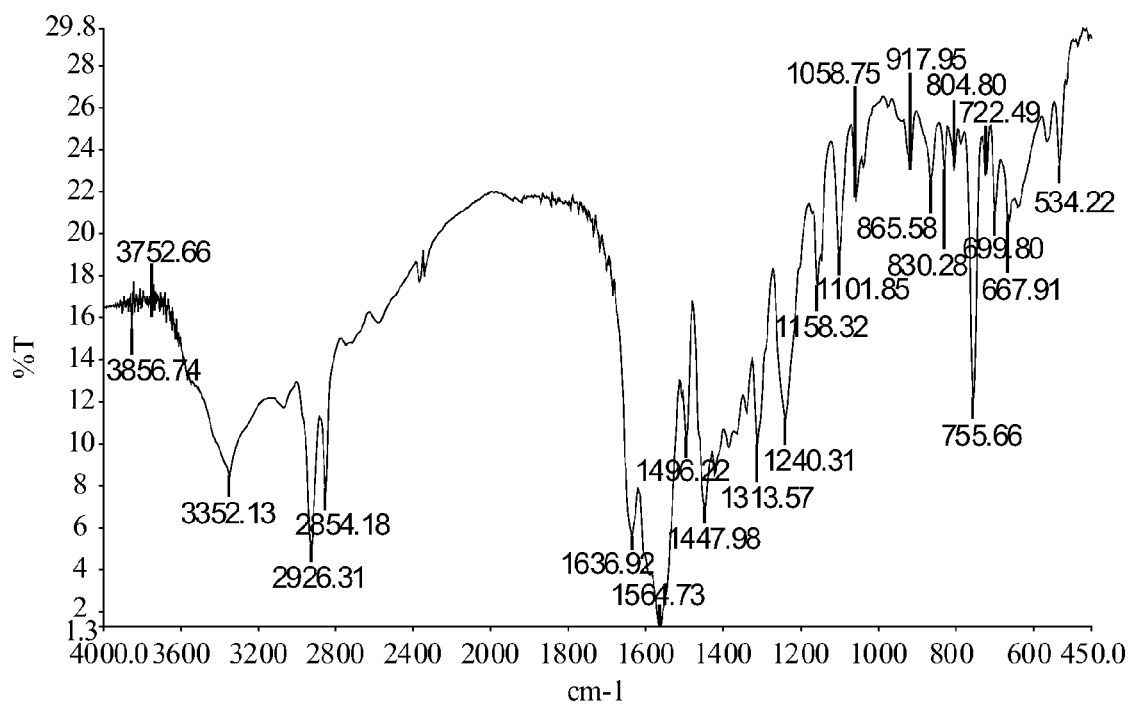
Figure 30:
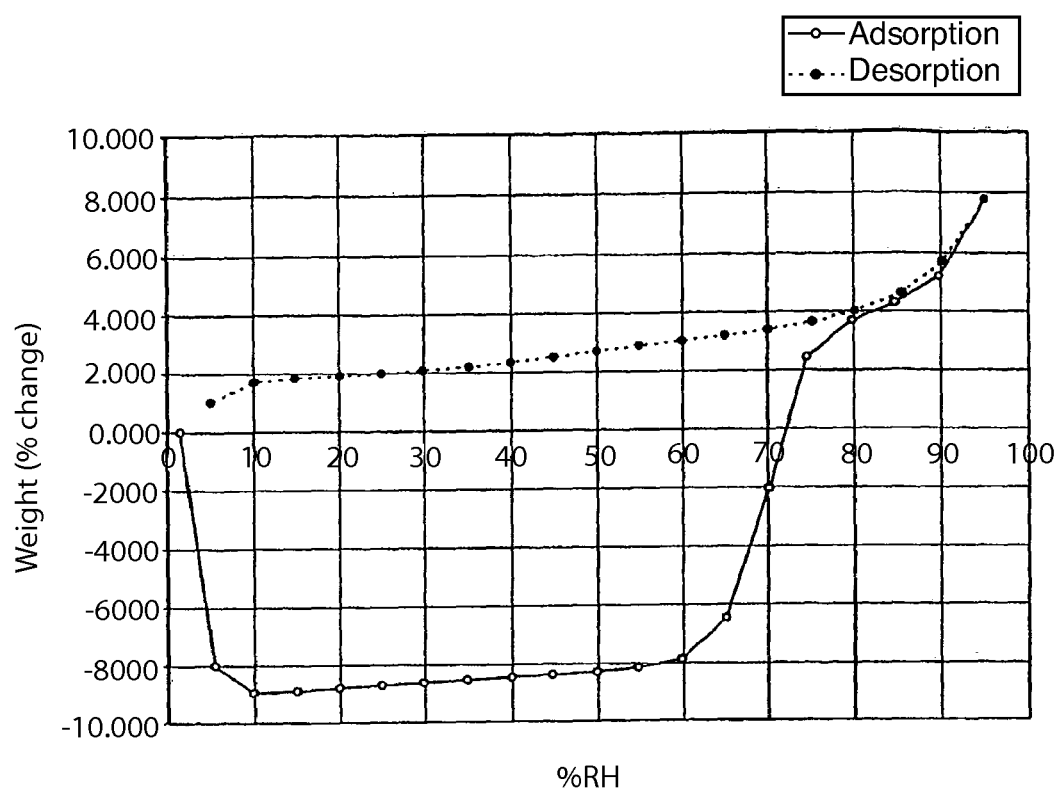

Crystalline polymorph Form VI of SNAC is an ethanol-water co-solvate (approximately 0.6 moles of methanol and 2 moles of water per 1 mole of SNAC). According to differential scanning calorimetry (DSC), Form VI has a melting point onset at about 197° C. (see FIG. 27). Form VI of SNAC has an XRPD pattern substantially identical to that shown in FIG. 26. Characteristic XRPD peak locations (expressed in degrees 2θ±0.2, 0.1, 0.05, or 0.01° 2θ) and d-spacing for Form V are provided in Table 6 below. The XRPD peak locations marked "(U)" in Table 6 are unique to Form VI. For example, the peaks at 9.60, 10.43, 12.68, and 16.58° 2θ±0.2, 0.1, 0.05, or 0.01° 2θ are unique to Form VI.

TABLE 6

Characteristic XRPD Peaks (expressed in degrees 2θ) of Form VI of SNAC

| Degrees 2θ ± 0.2° 2θ | d (Å) |
|---|---|
| 5.68 U | 15.55 |
| 6.35 U | 13.91 |
| 6.72 | 13.13 |
| 9.60 U | 9.20 |
| 10.43 U | 8.47 |
| 11.31 | 7.82 |
| 12.68 U | 6.97 |
| 14.95 U | 5.92 |
| 16.58 U | 5.34 |
| 17.46 U | 5.08 |
| 18.12 U | 4.89 |
| 18.96 U | 4.68 |
| 19.37 | 4.58 |
| 19.88 U | 4.46 |
| 20.95 U | 4.24 |
| 21.54 U | 4.12 |
| 22.08 U | 4.02 |
| 22.36 U | 3.97 |
| 22.95 | 3.87 |
| 23.76 U | 3.74 |
| 24.24 U | 3.67 |
| 25.08 U | 3.55 |
| 25.56 U | 3.48 |
| 26.98 U | 3.30 |
| 27.36 U | 3.26 |
| 28.68 U | 3.11 |
| 29.35 U | 3.04 |
| 30.48 U | 2.93 |
| 30.84 U | 2.89 |
| 31.91 | 2.80 |
| 34.00 U | 2.63 |
| 36.16 U | 2.48 |
| 38.32 U | 2.34 |

Form VI may be prepared by crystallization of SNAC (e.g., Forms I-V or a mixture thereof) from an ethanol solution at a relative humidity of at least about 30, 40 or 50%. For example, Form VI can be prepared by preparing a saturated solution of SNAC (e.g., Form I-V of SNAC or a mixture thereof) in ethanol at a relative humidity of at least about 30, 40, or 50% and cooling the resulting solution to room temperature or lower (e.g., in an ice bath). The resulting precipitate can then be filtered and dried.

Form VI may also be prepared by slurring any of Forms I-V in ethanol at a relative humidity of at least about 10, 20, or 30%. For example, Form VI can be prepared by adding any of Forms I-V to ethanol to form a precipitate, and maintaining the slurried mixture at ambient temperatures for a sufficient time to form Form VI (e.g., several days). The resulting solid may be recovered, e.g., by vacuum filtration and air-drying.

Amorphous SNAC

Amorphous SNAC is unstable at ambient conditions and converts to Form III upon exposure to humidity. Amorphous SNAC can be prepared by dehydrating Form III of SNAC (e.g., in a vacuum) for a sufficient time to form amorphous SNAC. Amorphous SNAC can also be prepared by dehydrating Form V or VI of SNAC (e.g., in a vacuum) for a sufficient time to form amorphous SNAC.

The crystals prepared by any of the aforementioned procedures may be recovered by any method known in the art.

Active Agents

Active agents suitable for use in the present invention include biologically active agents and chemically active agents, including, but not limited to, pesticides, pharmacological agents, and therapeutic agents.

Suitable biologically and chemically active agents include, but are not limited to, proteins; polypeptides; peptides; hormones; polysaccharides, muco-polysaccharides and particularly mixtures of muco-polysaccharides; carbohydrates; lipids; small polar organic molecules (i.e. polar organic molecules having a molecular weight of 500 daltons or less); other organic compounds; and particularly compounds which by themselves do not pass (or which pass only a fraction of the administered dose) through the gastro-intestinal mucosa and/or are susceptible to chemical cleavage by acids and enzymes in the gastro-intestinal tract; or any combination thereof.

Further examples of suitable biologically active agents include, but are not limited to, the following, including synthetic, natural or recombinant sources thereof: growth hormones, including human growth hormones (hGH), recombinant human growth hormones (rhGH), bovine growth (hGH), bovine growth hormones, and porcine growth hormones; growth hormone-releasing hormones; growth hormone releasing factor (e.g., GRF analog g); interferons, including α, β and γ; interleukin-1; interleukin-2; insulin, including porcine, bovine, human, and human recombinant, optionally having counter ions including zinc, sodium, calcium and ammonium; insulin-like growth factor, including IGF-1; heparin, including unfractionated heparin, heparinoids, dermatans, chondroitins, low molecular weight heparin, very low molecular weight heparin and ultra low molecular weight heparin; calcitonin, including salmon, eel, porcine and human; erythropoietin; atrial naturetic factor; antigens; monoclonal antibodies; somatostatin; protease inhibitors; adrenocorticotropin, gonadotropin releasing hormone; oxytocin; leutinizing-hormone-releasing-hormone; follicle stimulating hormone; glucocerebrosidase; thrombopoietin; filgrastim; prostaglandins; cyclosporin; vasopressin; cromolyn sodium (sodium or disodium chromoglycate); vancomycin; desferrioxamine (DFO); bisphosphonates, including ibandronate, alendronate, tiludronate, etidronate, clodronate, pamidronate, olpadronate, and incadronate, and pharmaceutically acceptable salts thereof (e.g., ibandronate sodium); gallium salts (such as gallium nitrate, gallium nitrate nonahydrate, and gallium maltolate); acyclovir and pharmaceutically acceptable salts thereof (e.g., acyclovir sodium); parathyroid hormone (PTH), including its fragments; anti-migraine agents such as BIBN-4096BS and other calcitonin gene-related proteins antagonists; antimicrobials, including antibiotics (include gram-positive acting, bacteriocidal, lipopeptidal and cyclic peptidal antibiotics, including daptomycin), antibacterials and anti-fungal agents; vitamins; analogs, fragments, mimetics or polyethylene glycol (PEG)-modified derivatives of these compounds; or any combination thereof.

According to one embodiment, the active agent is ibandronate or a pharmaceutically acceptable salt thereof (e.g., ibandronate sodium). According to the another embodiment, the active agent is gallium salt, such as gallium nitrate or gallium nitrate nonahydrate. According to yet another embodiment, the active agent is acyclovir or a pharmaceutically acceptable salt thereof (e.g., acyclovir sodium). According to yet another embodiment, the active agent is heparin. According to yet another embodiment, the active agent is insulin.

Pharmaceutical Compositions

The pharmaceutical composition is preferably in solid form and may be formed into a solid dosage form. The solid dosage form can be a capsule, tablet or particle, such as a powder or sachet. The powder may be in the form of a sachet that is mixed with a liquid and administered. The solid dosage form may also be a topical delivery system, such as an ointment, cream or semi-solid. The solid dosage form contemplated may include a sustained release or controlled release system. Preferably, the solid dosage form is for oral administration.

The powder may be packed into capsules, or pressed into tablets, used in powder form, or incorporated into an ointment, cream or semi-solid. Methods for forming solid dosage forms are well known in the art.

The amount of delivery agent in the solid dosage form is a delivery effective amount and can be determined for any particular compound or biologically or chemically active agent by methods known to those skilled in the art.

Following administration, the active agent in the dosage unit form is taken up into circulation. The bioavailability of the active agent is readily assessed by measuring a known pharmacological activity in blood, e.g. an increase in blood clotting time caused by heparin, or a decrease in circulating calcium levels caused by calcitonin. Alternately, the circulating levels of the active agent itself can be measured directly.

The solid dosage form may include pharmaceutically acceptable additives, such as excipients, carriers, diluents, stabilizers, plasticizers, binders, glidants, disintegrants, bulking agents, lubricants, plasticizers, colorants, film formers, flavouring agents, preservatives, dosing vehicles, surfactants, and any combination of any of the foregoing. Preferably, these additives are pharmaceutically acceptable additives, such as those described in *Remington's, The Science and Practice of Pharmacy*, (Gennaro, A. R., ed., 19th edition, 1995, Mack Pub. Co.) which is herein incorporated by reference.

Suitable binders include, but are not limited to, starch, gelatine, sugars (such as sucrose, molasses and lactose), dibasic calcium phosphate dihydrate, natural and synthetic gums (such as acacia, sodium alginate, carboxymethyl cellulose, methyl cellulose, polyvinylpyrrolidone, polyethylene glycol, ethylcellulose, and waxes.

Suitable glidants include, but are not limited to, talc, and silicon dioxide (silica) (e.g., fumed silica and colloidal silicon dioxide).

Suitable disintegrants include, but are not limited to, starches, sodium starch glycolate, croscarmellose sodium, crospovidone, clays, celluloses (such as purified cellulose, methylcellulose, sodium carboxymethyl cellulose), alginates, pregelatinized corn starches, and gums (such as agar, guar, locust bean, karaya, pectin and tragacanth gums). A preferred disintegrant is sodium starch glycolate.

Suitable bulking agents include, but are not limited to, starches (such as rice starch), microcrystalline cellulose, lactose (e.g., lactose monohydrate), sucrose, dextrose, mannitol, calcium sulfate, dicalcium sulfate, and tricalcium sulfate.

Suitable lubricants include, but are not limited to, stearic acid, stearates (such as calcium stearate and magnesium stearate), talc, boric acid, sodium benzoate, sodium acetate, sodium fumarate, sodium chloride, polyethylene glycol, hydrogenated cottonseed, and castor oils.

Suitable surfactants include, but are not limited to, sodium lauryl sulfate, hydroxylated soy lecithin, polysorbates, and block copolymers of propylene oxide and ethylene oxide.

Delivery Systems

The amount of active agent used in a pharmaceutical composition of the present invention is an amount effective to accomplish the purpose of the particular active agent for the target indication. The amount of active agent in the compositions typically is a pharmacologically, biologically, therapeutically, or chemically effective amount. However, the amount can be less than that amount when the composition is used in a dosage unit form because the dosage unit form may contain a plurality of delivery agent compound/active agent compositions or may contain a divided pharmacologically, biologically, therapeutically, or chemically effective amount. The total effective amount can then be administered in cumulative units containing, in total, an effective amount of the active agent.

The total amount of active agent to be used can be determined by methods known to those skilled in the art. However, because the compositions of the invention may deliver active agents more efficiently than other compositions or compositions containing the active agent alone, lower amounts of biologically or chemically active agents than those used in prior dosage unit forms or delivery systems can be administered to the subject, while still achieving the same blood levels and/or therapeutic effects.

Generally, the weight ratio of delivery agent to active agent ranges from about 0.1:1 to about 1000:1 and preferably from about 1:1 to about 300:1. The weight ratio will vary according to the active agent and the particular indication for which the active agent is administered.

The presently disclosed delivery agents facilitate the delivery of biologically and chemically active agents, particularly in oral, sublingual, buccal, intraduodenal, intracolonic, rectal, vaginal, mucosal, pulmonary, intranasal, and ocular systems.

The compounds and compositions of the subject invention are useful for administering biologically or chemically active agents to any animals, including but not limited to birds such as chickens; mammals, such as rodents, cows, pigs, dogs, cats, primates, and particularly humans; and insects.

The compounds and compositions are particularly advantageous for delivering chemically or biologically active agents that would otherwise be destroyed or rendered less effective by conditions encountered before the active agent reaches its target zone (i.e. the area in which the active agent of the delivery composition is to be released) and within the body of the animal to which they are administered. Particularly, the compounds and compositions of the present invention are useful in orally administering active agents, especially those that are not ordinarily orally deliverable, or those for which improved delivery is desired.

The compositions comprising the compounds and active agents have utility in the delivery of active agents to selected biological systems and in an increased or improved bioavailability of the active agent compared to administration of the active agent without the delivery agent. Delivery can be improved by delivering more active agent over a period of time, or in delivering active agent in a particular time period (such as to effect quicker or delayed delivery) or over a period of time (such as sustained delivery).

Another embodiment of the present invention is a method for the treatment or prevention of a disease or for achieving a desired physiological effect, such as those listed in the table below, in an animal by administering the composition of the present invention. Specific indications for active agents can be found in the Physicians' Desk Reference ($54^{th}$ Ed., 2000, Medical Economics Company, Inc., Montvale, N.J.), which is herein incorporated by reference. The active agents in the table below include their analogs, fragments, mimetics, and polyethylene glycol-modified derivatives.

| Active Agent | Disease and Physiological Effect |
| --- | --- |
| Growth hormones, including human growth hormones (hGH), recombinant human growth hormones (rhGH), bovine growth hormones, and porcine growth hormones; growth hormone-releasing hormones. | Growth disorders |
| Interferons, including $\alpha$, $\beta$ and $\gamma$. | Viral infection, including chronic cancer and multiple sclerosis |

| Active Agent | Disease and Physiological Effect |
|---|---|
| Interleukin-1; interleukin-2. | Viral infection; cancer |
| Insulin, including porcine, bovine, human, and human recombinant, optionally having counter ions including zinc, sodium, calcium and ammonium; insulin-like growth factor, including IGF-1. | Diabetes |
| Heparin, including unfractionated heparin, heparinoids, dermatans, chondroitins, low molecular weight heparin, very low molecular weight heparin and ultra low molecular weight heparin. | Thrombosis; prevention of blood coagulation |
| Calcitonin, including salmon, eel, porcine and human. | Osteoporosis; diseases of the bone |
| Erythropoietin | Anemia |
| Atrial naturetic factor | Vasodilation |
| Antigens | Infection |
| Monoclonal antibodies | To prevent graft rejection; cancer |
| Somatostatin | Bleeding ulcer; erosive gastritis |
| Protease inhibitors | AIDS |
| Adrenocorticotropin | High cholesterol (to lower cholesterol) |
| Gonadotropin releasing hormone | Ovulatory disfunction (to stimulate ovulation) |
| Growth Hormone Releasing Factor (GRF) | stimulates the secretion of the growth hormone |
| Oxytocin | Labor disfunction (to stimulate contractions) |
| Leutinizing-hormone-releasing-hormone; follicle stimulating hormone | Regulate reproductive function |
| Glucocerebrosidase | Gaucher disease (to metabolize lipoprotein) |
| Thrombopoietin | Thrombocytopenia |
| Filgrastim | Reduce infection in chemotherapy patients |
| Prostaglandins | Hypertension |
| Cyclosporin | Transplant rejection |
| Vasopressin | Bed-wetting; antidiuretic |
| Cromolyn sodium (sodium or disodium chromoglycate); vancomycin | Asthma; allergies |
| Desferrioxamine (DFO) | Iron overload |
| Parathyroid hormone (PTH), including its fragments. | Osteoporosis; diseases of the bone |
| Antimicrobials, including antibiotics, anti-bacterials and anti-fungal agents; gram-positive acting, bacteriocidal, lipopeptidal and cyclic peptidal antibiotics, and includes daptomycin and analogues thereof | Infection including gram-positive bacterial infection |
| Vitamins | Vitamin deficiencies |
| Bisphosphonates, including ibandronate, alendronate, tiludronate, etidronate, clodronate, pamidronate, olpadronate, and incadronate | Osteoporosis and Paget's disease; Inhibits osteoclasts |
| Gallium salts (e.g., gallium nitrate) | Treats or prevents hypercalcemia. Treats or prevents a disorder associated with excessive (or accelerated) loss of calcium from bone in a mammal (such as a human) by administering to the mammal an effective amount of the pharmaceutical formulation of the present invention. Such disorders include, but are not limited to, hypercalcemia, osteopenia, osteoporosis, bone destruction due to metastasis from malignant tumors, hyperparathyroidism, renal disease, iatrogenic disease (including drug-induced diseases), and periodontal disease. Inhibits resorption or release of calcium from bone. |
| Acyclovir | Treats virus infections, especially herpes infections such as herpes simplex 1 and 2 viruses (HSV 1, HSV 2), varicella zoster virus (VZV), cytomegalovirus (CMV) and Epstein-Barr virus (EBV), and other herpes virus infections (e.g. feline herpes virus infections). Treats clinical conditions or symptoms which are caused by the viruses enumerated above, including herpetic karatitis, herpetic encaphalitis, cold sores and genital infections (caused by herpes simplex), chicken pox and shingles (caused by varicella zoster) and CMV-pneumonia and retinitis, particularly in immunocompromised patients including renal and bone marrow transplant patients and patients with Acquired Immune Deficiency Syndrome (AIDS) by administering an effective amount of the composition or dosage unit form of the present invention. Epstein-Barr virus (EVB) causes infectious mononucleosis, and is also suggested as the causative agent of nasopharyngeal cancer, immunoblastic lymphoma, Burkitt's lymphoma and hairy leukoplakia. |

The following examples illustrate the present invention without limitation. All percentages are by weight unless otherwise specified.

DSC

The melting points cited were determined by differential scanning calorimety (DSC). The quoted values were obtained with Perkin Elmer Pyris 1 software for Windows. The instrument was calibrated for temperature using the melting points of indium and zinc, and for enthalpy using the enthalpy of fusion of indium. Calibration checks were performed on a routine basis using an indium standard. Samples were sealed in an aluminum pan with a crimped lid that had a tiny hole in it. The samples were then heated in a nitrogen atmosphere from 30 to 250° C. at 10° C./min Un-milled samples were lightly ground with a mortar and pestle prior to analysis in order to improve thermal contact with the surfaces of the sample pan.

XRPD

The Powder X-Ray diffraction analysis was done using a Shimadzu XRD-6000 powder diffractometer, available from Shimadzu Scientific Instruments, Inc. of Columbia, Md. The instrument was calibrated using silicon powder, and the calibration was found to be correct when it was tested with an NIST #675 low-angle diffraction standard. The samples were illuminated with Cu K∀ radiation (8=1.54056 Å). Un-milled samples were lightly ground with a mortar and pestle so that a sample could be prepared for analysis with a smooth, even, surface. The diffraction pattern between 2 and 40° 22 was used as a fingerprint region to identify the crystal structure present in the lots.

Thermogravimetric Analysis (TGA)

Thermogravimetric analysis of sodium 4-CNAB was conducted using a Perkin-Elmer TGA7 thermogravimetric analyzer with Pyris 1 for Windows software. The instrument was calibrated for temperature using the curie points of alumel and nickel. Samples were heated in a nitrogen atmosphere from 30 to 300° C. and the percent change in weight as a function of temperature was recorded. The un-milled lots were lightly ground with a mortar and pestle prior to analysis in order to decrease the effect of particle size and improve contact with the inner surfaces of the platinum sample holder.

Water Sorption-Desorption Behavior

Sorption analysis was conducted using an SGA-100 Symmetric Vapor Sorption Analyzer (available from VTI Corporation of Hialeah, Fla.). The instrument was calibrated using PVP and NaCl. Samples (other than solvates) were dried to constant weight at 60° C. prior to analysis. Samples of solvates were not dried prior to testing. The equilibrium water content of the sample from 5% relative humidity (RH) to 95% RH and then back down to 5% RH was determined at 25° C.

FTIR

FTIR was performed on a Perkin Elmer Spectrum BX FT-IR using KBr discs. 1 mg of sample was dispersed in 150 mg KBr. The resolution was 4 cm$^{-1}$ and 32 scans were averaged.

Example 1

Preparation for Form I of SNAC

Form I of SNAC was prepared as follows. The free acid of SNAC (i.e. N-(8-[2-hydroxybenzoyl]amino)caprylic acid) was prepared by the method described in Example 1 of International Publication No. WO 00/59863, which is hereby incorporated by reference in its entirety, using the appropriate starting materials.

Form I of SNAC was prepared from the free acid of SNAC by the following procedure, which is also described in Example 12 of International Publication No. WO 00/59863.

Into a clean 300 gallon reactor was charged 321 L of ethanol, which was denatured with 0.5% toluene. While stirring, 109 kg (dry) of the free acid of SNAC was added. The reactor was heated to 28° C. and maintained at a temperature above 25° C. A solution of 34 L purified water, USP and 15.78 kg sodium hydroxide was prepared, cooled to 24° C., and added to the stirring reactor over 15 minutes, keeping the reaction temperature at 25-35° C. The mixture was stirred for an additional 15 minutes.

Into an adjacent reactor was charged 321 L of ethanol, which was denatured with 0.5% toluene. The reactor was heated to 28° C. using a circulator. The solution from the first reactor was added to the second reactor over 30 minutes, keeping the temperature above 25° C. The contents were stirred and 418 L of heptane was added. The reaction mixture was cooled to 10° C., centrifuged and then washed with 60 L of heptane. The product was collected and dried in a Stokes oven at 82° C. under 26" Hg vacuum for about 65 hours (over a weekend). 107.5 kg monosodium SNAC (i.e. the monosodium salt of N-(8-[2-hydroxybenzoyl]-amino)caprylic acid) was recovered.

XRPD, DSC, TGA, FTIR, and sorption/desorption spectra for Form I are shown in FIGS. 1-5, respectively.

Example 2

Preparation for Form II of SNAC

Form II of SNAC was prepared as follows. The procedure in Example 1 was repeated except for the last drying step. The SNAC ethanol solvate obtained was then dried in a tumble dryer and agglomerated (formed balls). The dryer lacked an internal agitation device. The SNAC was removed from the tumble dryer, milled with a Comil® milling machine (available from Quadro Engineering Inc. of Waterloo, Ontario, Canada), and tray dried. The SNAC was stored for at least 3 years in a double lined polyethylene bag which was placed in a stainless steel drum.

XRPD, DSC, TGA, FTIR, and sorption/desorption spectra for Form II are shown in FIGS. 6-10, respectively.

Example 3

Preparation for Form III of SNAC

Form III was prepared by exposing Form I of SNAC to a 90% relative humidity environment until Form I could not be detected by XRPD. The material was then allowed to dry under a hood until the moisture content was about 15% w/w.

XRPD, DSC, TGA, FTIR, and sorption/desorption spectra for Form III are shown in FIGS. 11-15, respectively.

Example 4

Preparation for Form IV of SNAC

Form IV was prepared by heating Form II for 3 hours in a dry air oven at 170° C. The Form IV prepared had a melting point onset according to DSC of about 198° C., and XRPD, DSC, TGA, FTIR, and sorption/desorption spectra as shown in FIGS. 16-20.

Example 5

Preparation for Form V of SNAC

Form V of SNAC was prepared by slurring Form I of SNAC in methanol for a week. The resulting precipitate was vacuum filtered and air-dried for an hour. The Form V prepared had a melting point onset according to DSC of about 197° C., and XRPD, DSC, TGA, FTIR, and sorption/desorption spectra as shown in FIGS. 21-25.

Example 6

Method of Preparation for Form VI of SNAC

Form VI was prepared by slurring Form I in ethanol for a week. The resulting precipitate was vacuum filtered and air-dried for an hour. The Form VI prepared had a melting point onset according to DSC of about 197° C., and an XRPD, DSC, TGA, FTIR, and sorption/desorption spectra as shown in FIGS. 26-30.

Example 7

Preparation of Capsules Containing Form I or III of SNAC and Heparin USP

Capsules (size 1, available from Capsugel of Morris Plains, N.J.) containing SNAC (Form I or III) and heparin USP (30,000 IU) as shown in Table 7 were prepared as follows. SNAC (Form I or III as prepared in Examples 1 and 3) and heparin were screened through mesh #35. The specified amount of heparin and SNAC were weighed and transferred to a clean, dry glass 8 oz mortar. A volume of SNAC equivalent to the volume of heparin was added to the mortar and mixed with a pestle for 2 minutes. The remainder of the SNAC was added to the mixture and mixed again for 2 minutes. Capsules containing the appropriate amount of were filled.

TABLE 7

| Ingredients | SNAC (Form I) Capsule Quantity per capsule (mg) | SNAC (Form III) Capsule Quantity per capsule (mg) |
|---|---|---|
| SNAC | 153.33 | 181.72[1] |
| Heparin USP | 56.82 | 56.82 |

[1]Assuming Form III of SNAC is a trihydrate, about 15.62% (28.39 mg) of Form III is water and the remaining 84.38% (153.33 mg) is SNAC (on an anhydrous basis).

Administration to Cynos Monkeys

Cynomolgus monkeys (average weight of 4.1 kg for males and 3.0 kg for females) were fasted for at least 24 hours prior to dosing. 3 SNAC/heparin capsules were inserted at the tip of a tubing, and air flushed to discharge the capsules into the stomach. Food was given back 2 hours after dosing. Water was available at all times. Approximately 1.3 ml of whole blood was collected into citrated tubes at pre-dose, and at 10, 20, 30 and 50 minutes, and 1, 1.5, 2, 3, 4 and 6 hours post dosing. The blood samples were centrifuged for 10 minutes at 2500 RPM and 250 µL of the resulting plasma was used with a factor Xa assay using an Organon Teknika COAG-A-MATE MTX/MTX II machine. The standard range for the assay was 0-2 IU/mL of heparin.

Figures 31, 32:
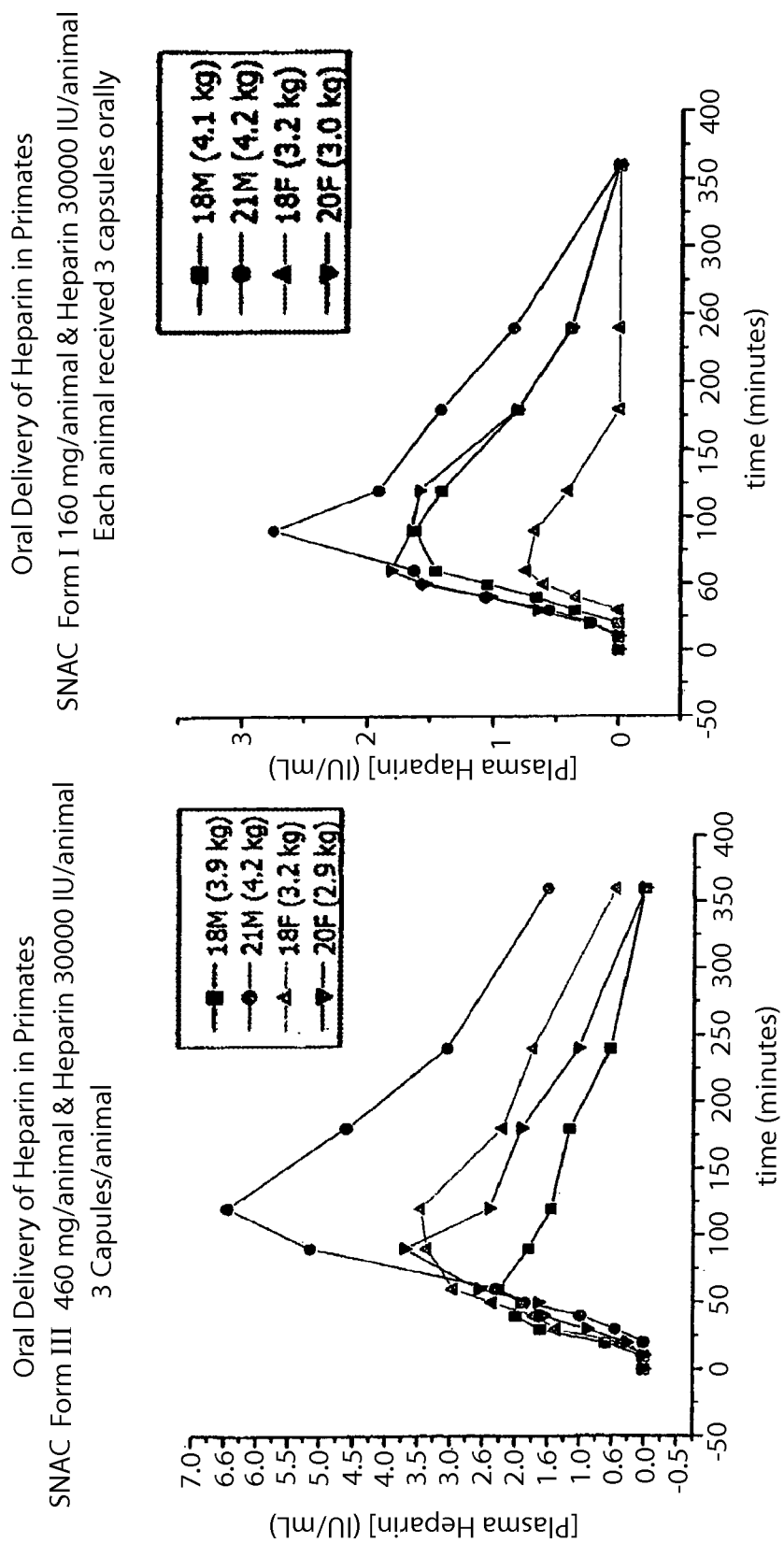
FIGS. 31 and 32 are graphs of the plasma heparin concentrations in cynos monkeys versus time after oral administration of capsules of Form I or III of SNAC and heparin as prepared in Example 7.
Figure 33:
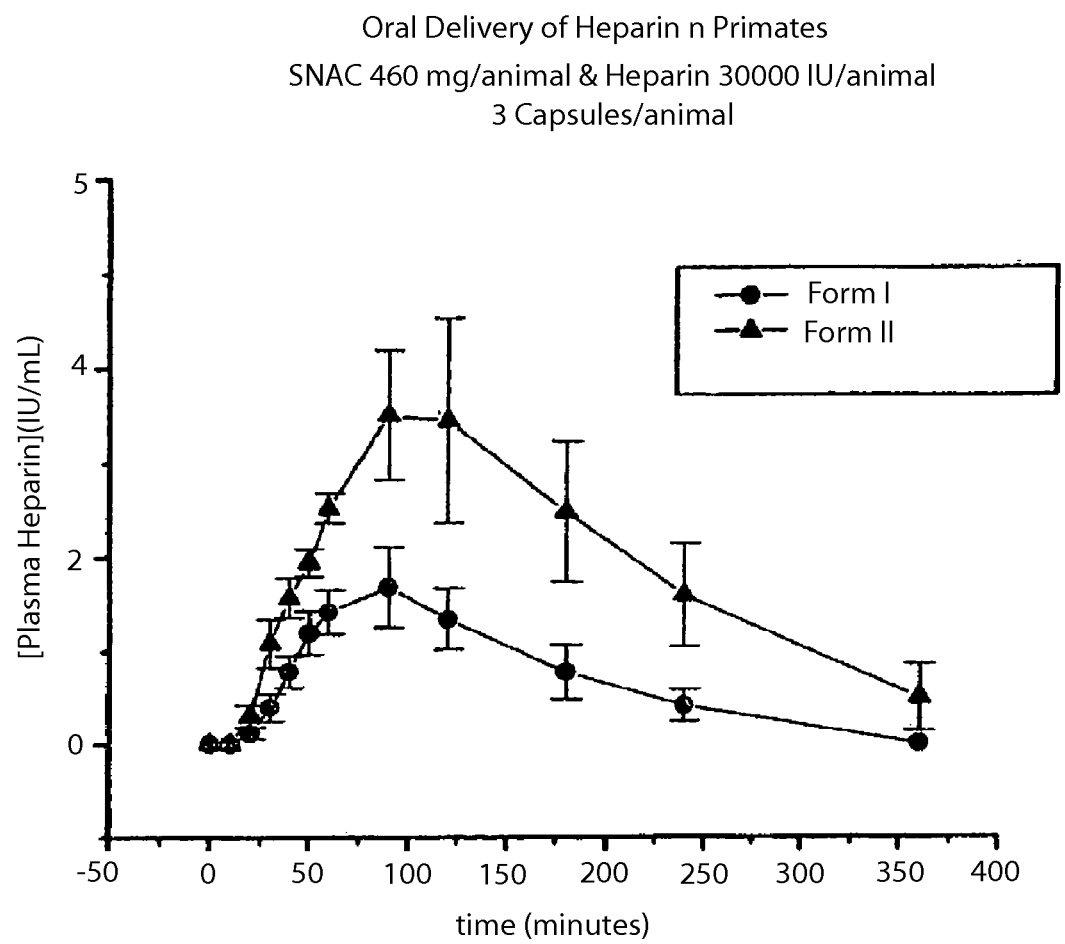
FIG. 33 is a graph of the plasma heparin concentrations in cynos monkeys versus time after oral administration of capsules of Form I or III of SNAC and heparin as prepared in Example 7.

The results for Forms I and III of SNAC with heparin are shown in FIGS. 31 and 32, respectively. The results were averaged for monkeys by sex and weight. In other words, there are data points for 4 monkeys (a 3.9 kg male, 4.2 kg male, 3.2 kg female, and 2.9 kg female). The results for each form of SNAC at each time point for all the monkeys were averaged and are shown in FIG. 33.

Example 8

Preparation of Capsules Containing Form I or III of SNAC and Heparin USP

Capsules (size 1, available from Capsugel of Morris Plains, N.J.) containing SNAC (Form I or III) and heparin USP (30,000 IU) as shown in Table 7 above were prepared by the procedure described in Example 7.

Administration to Cynos Monkeys

The procedure described in Example 7 was repeated with 2 male monkeys having an average weight of 5.6 kg and 2 female monkeys having an average weight of 6.9 kg.

Figures 34, 35:
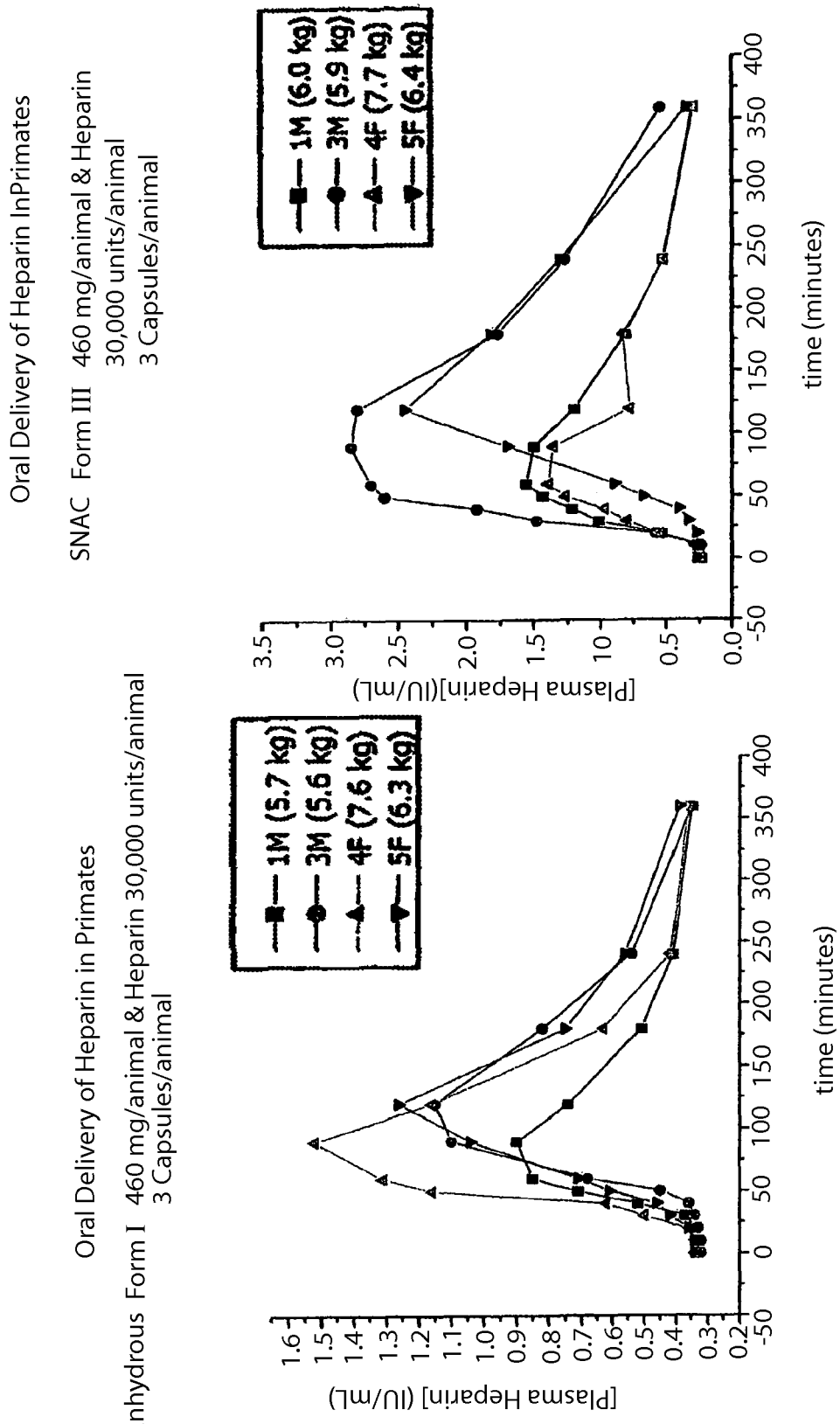
FIGS. 34 and 35 are graphs of the plasma heparin concentrations in cynos monkeys versus time after oral administration of capsules of Form I or III of SNAC and heparin as prepared in Example 8.
Figure 36:
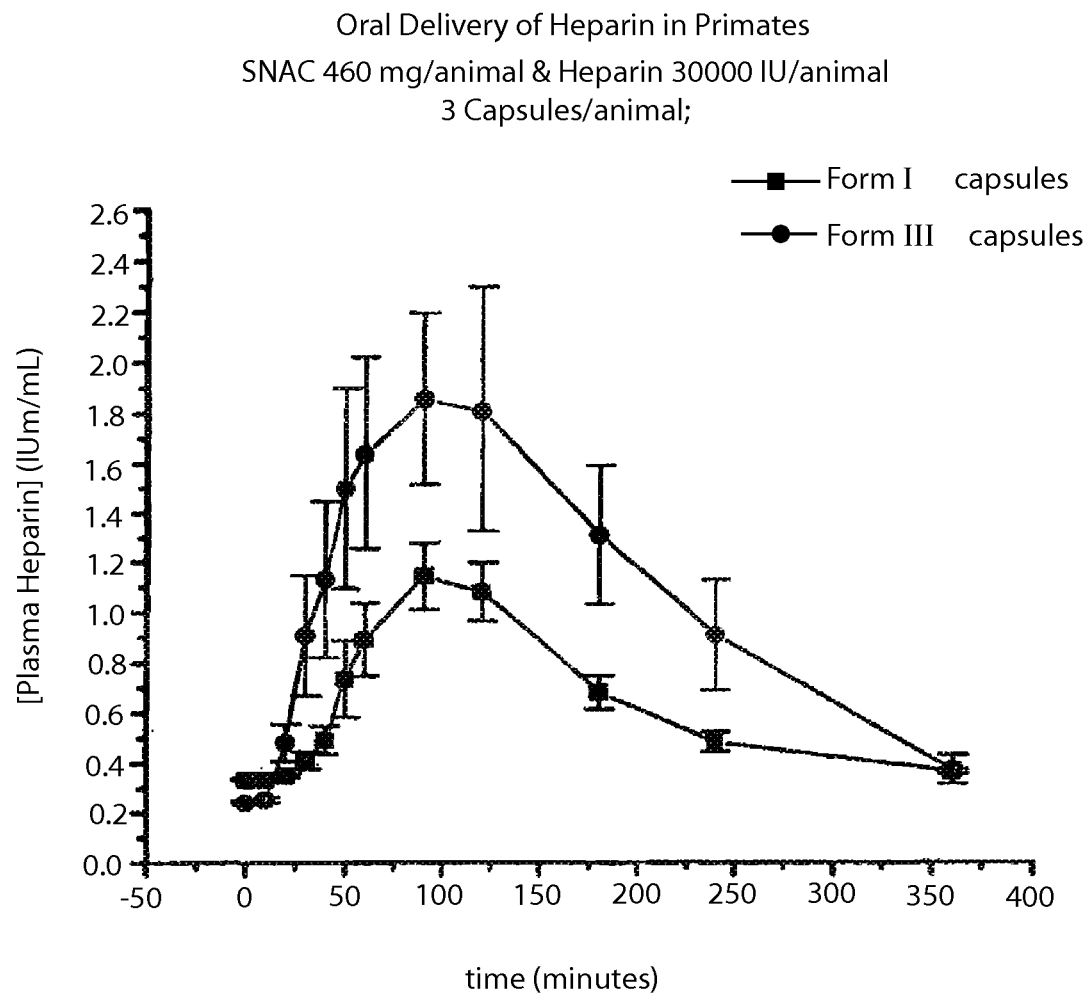
FIG. 36 is a graph of the plasma heparin concentrations in cynos monkeys versus time after oral administration of capsules of Form I or III of SNAC and heparin as prepared in Example 8.

The results for Forms I and III of SNAC with heparin are shown in FIGS. 34 and 35, respectively. The results were averaged for monkeys by sex and weight. In other words, there are data points for 4 monkeys (a 5.7 kg male, 5.6 kg male, 7.6 kg female, and 6.3 kg female). The results for each form of SNAC at each time point for all the monkeys were averaged and are shown in FIG. 36.

Example 9

The intrinsic dissolution rates for Forms I-IV of SNAC as prepared in Examples 1-4 were determined as follows.

The intrinsic dissolution rate of pellets of Forms I-IV was determined with a Wood's apparatus. A 300 mg pellet of Form I, II, III, or IV of SNAC was prepared in a die. The surface area of the pellet available to the dissolution medium was 0.484 $cm^2$. The pellet was compressed at 1200-1400 lbs on a Carver press to form discs. The die was then attached to the shaft of a dissolution apparatus. The die was rotated at 50 rpm and then immersed in 900 mL of degassed dissolution medium maintained at 37° C. (pH 6.3). The dissolution experiments were conducted in water and in triplicate. The samples were analyzed by UV-spectroscopy on-line at 297.5 nm. The intrinsic dissolution rates were determined from the initial linear portion of the dissolution profile under sink conditions.

Figure 37:
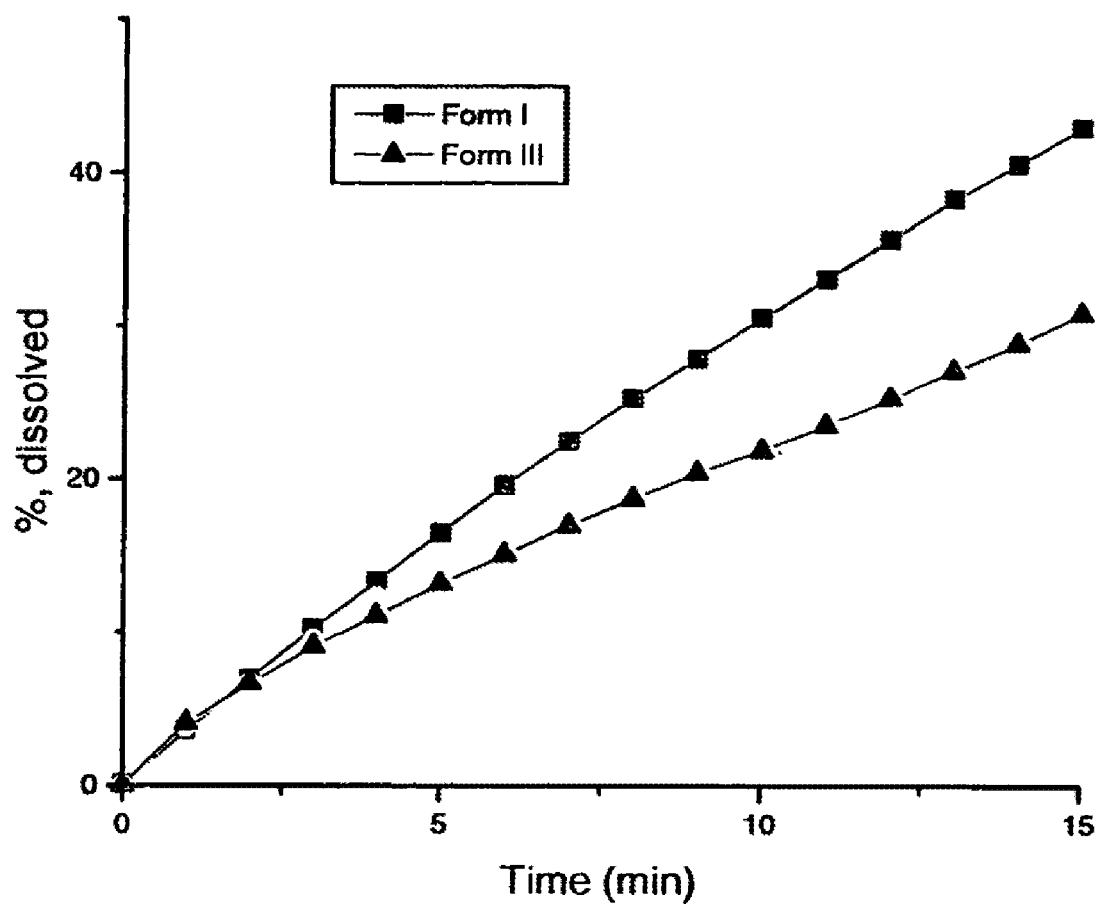
FIG. 37 is a graph of the amount by weight of a pellet of Form I or III of SNAC dissolved over 15 minutes in deionized water at 37° C. (Example 9).
Figure 38:
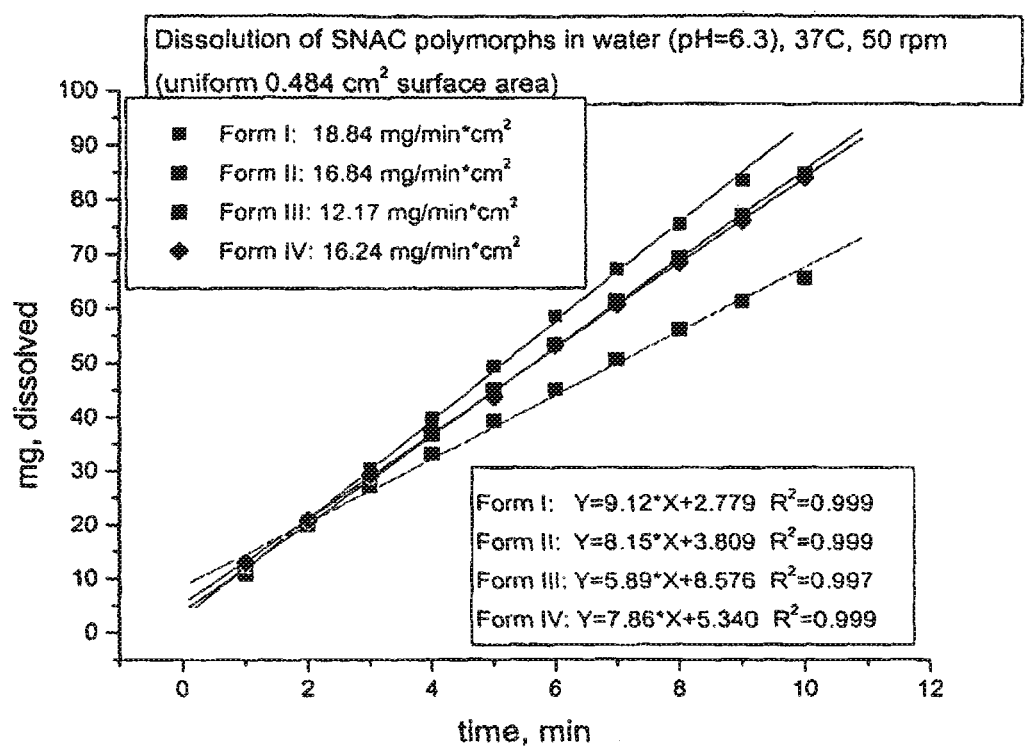
FIG. 38 is a graph of the amount by weight of a pellet of Form I, II, III, or IV of SNAC dissolved over 15 minutes in deionized water at 37° C. (Example 9).

The results are shown in FIGS. 37 and 38. The calculated dissolution rates for Forms I-IV are shown in Table 8 below.

TABLE 8

| Crystalline Form of SNAC | Calculated Dissolution Rate (mg/min · $cm^2$) |
|---|---|
| I | 18.84 ± 0.65 |
| II | 16.84 ± 0.08 |
| III | 12.17 ± 0.63 |
| IV | 16.24 ± 1.17 |

Example 10

The solubility of each of Forms I-IV of SNAC in acetonitrile was determined at ambient humidity and 25° C. Acetonitrile was chosen as a solvent since it is one of the few solvents in which SNAC is relatively poorly soluble, and the solutions can closely approach infinite dilution. The solubility data are shown in Table 9 below.

TABLE 9

| Crystalline Form of SNAC | Solubility (mg/mL) (±standard deviation) |
|---|---|
| I | 0.11 ± 0.01 |
| II | 0.08 ± 0.01 |
| III | 0.31 ± 0.02 |
| IV | 0.04 ± 0.01 |

Example 11

The effect of milling on Form I of SNAC was determined as follows. Milling was performed in a ball-mill Samples were withdrawn at after 20 hours and analyzed by XRPD.

Figure 39:
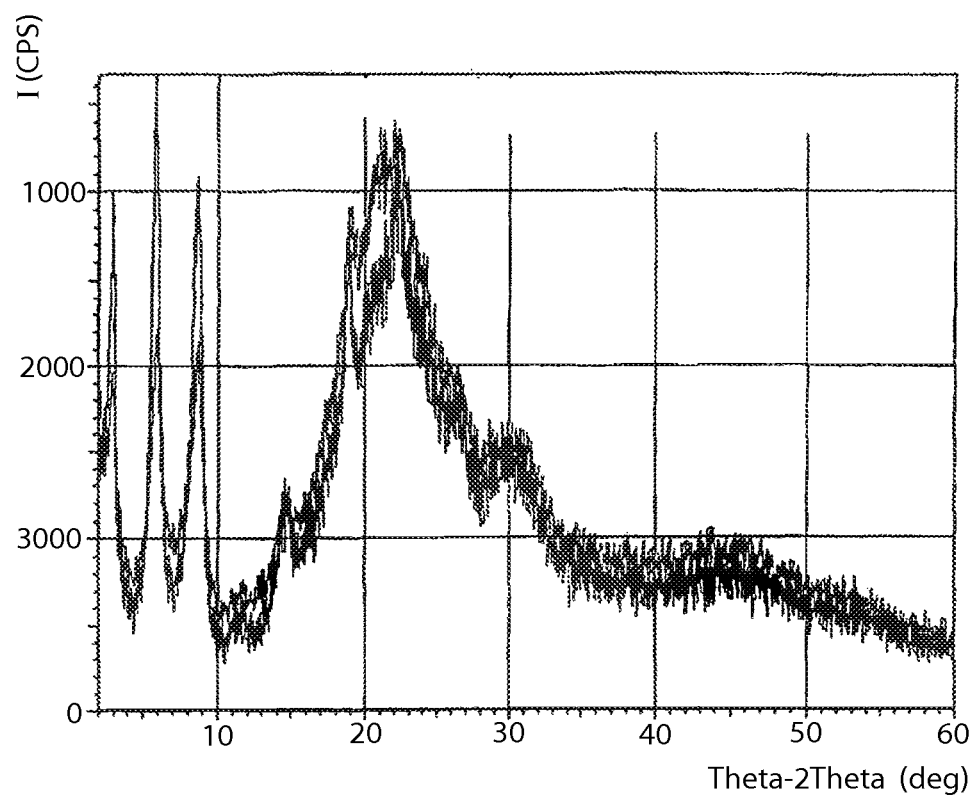
FIG. 39 shows XRPDs of Form I of SNAC before and after ball milling (Example 11).

The XRPD patterns of the SNAC samples before and after ball milling are substantially the same, as shown in FIG. 39.

Example 12

The effect of wet granulation on Form I of SNAC was determined as follows. Form I of SNAC was wet granulated manually in a glass mortar with a pestle as 20% w/w of water was added. The wet granules were analyzed by XRPD.

Figure 40:
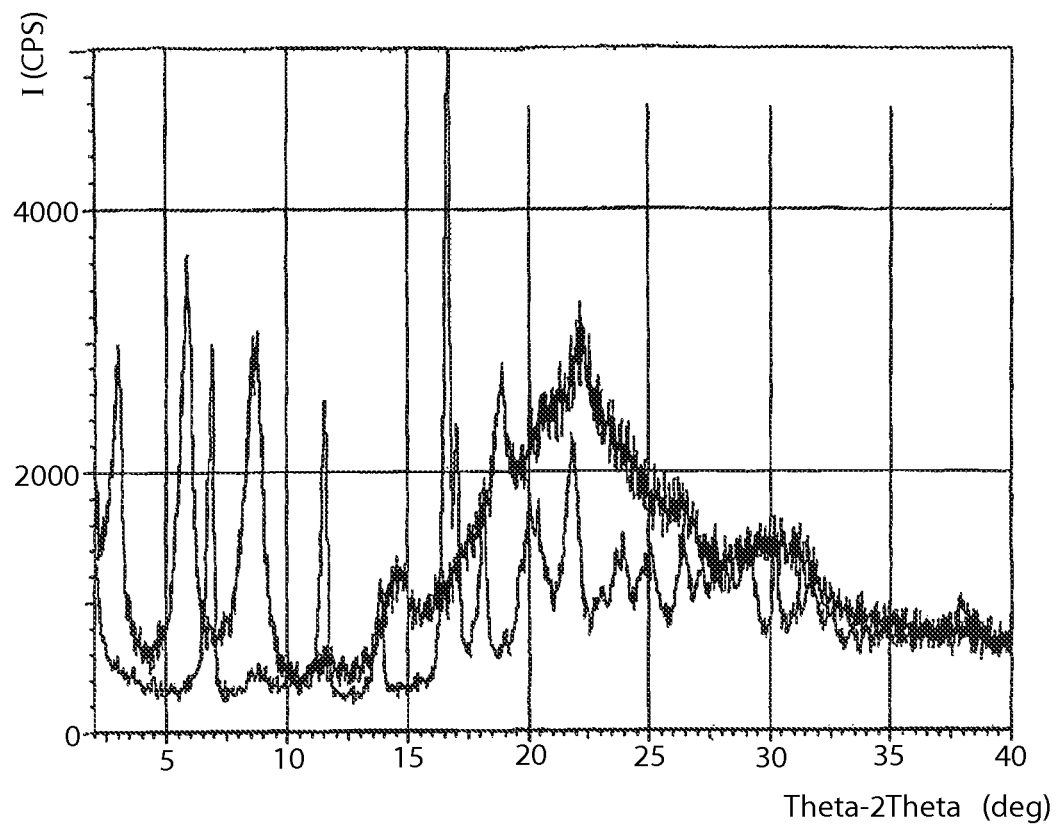
FIG. 40 shows XRPDs of Form I of SNAC before and after wet granulation (Example 12).

The XRPD patterns of the SNAC samples before and after wet granulation are shown in FIG. 40. The sample after wet granulation exhibits an XRPD pattern substantially the same as that for Form III.

Example 13

The effect of compression on Forms I and III of SNAC was evaluated as follows. Approximately 300 mg of each sample was compacted on a Carver press with 4500 lb force and 1 minute dwell time. The compression cycle was repeated 20 times. The crystal form of the SNAC in the composition was analyzed by XRPD.

Figure 41:
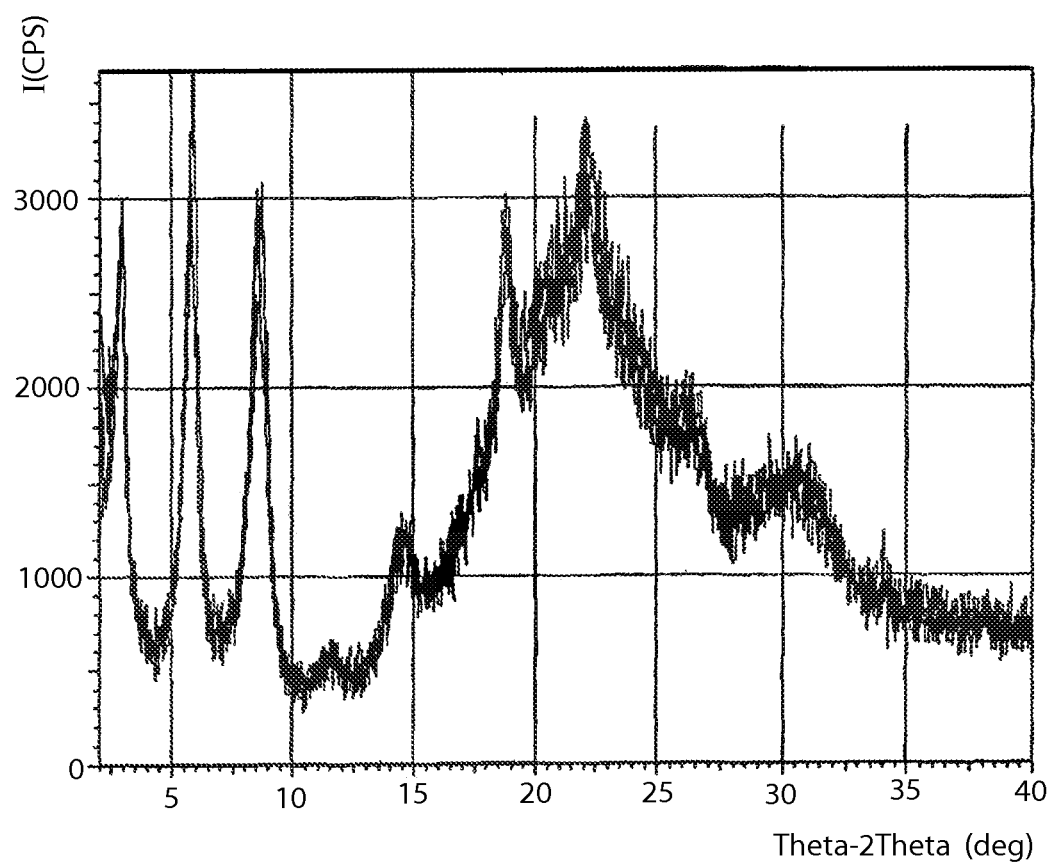
FIG. 41 shows XRPDs of Form I of SNAC before and after compression (Example 13).
Figure 42:
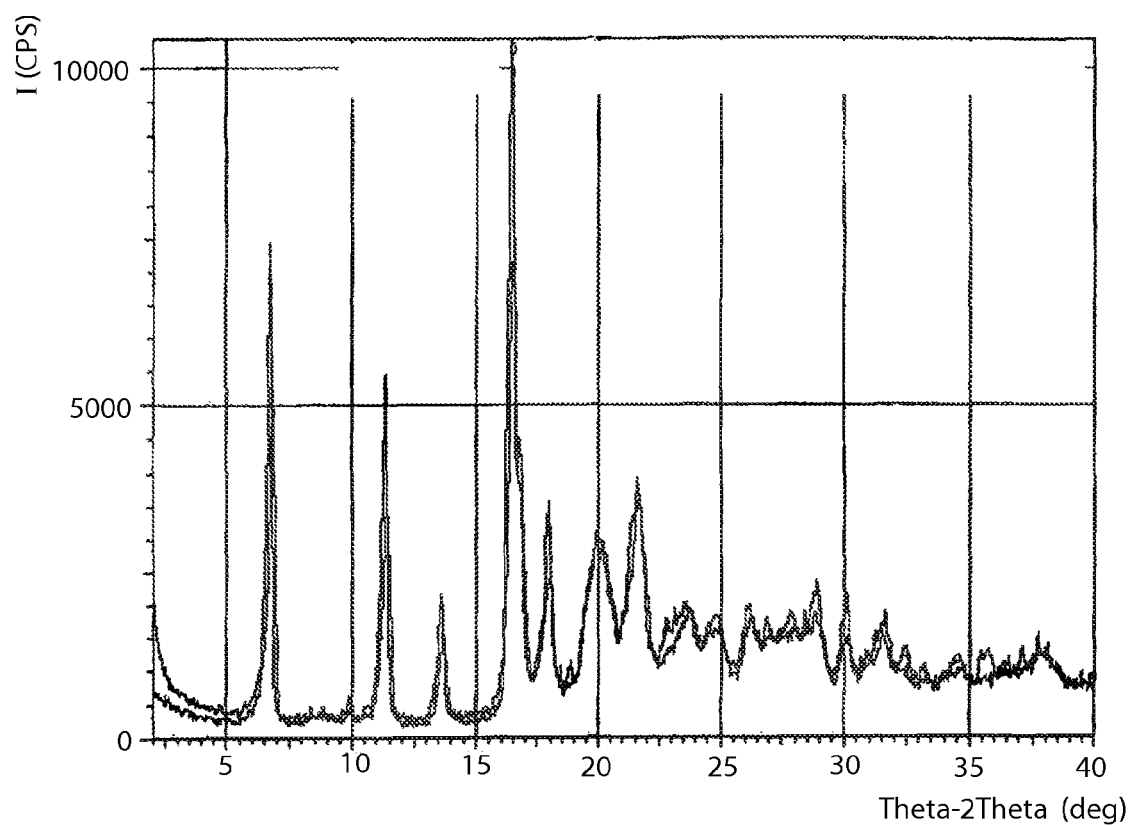
FIG. 42 shows XRPDs of Form III of SNAC before and after compression (Example 13).
Figure 43:
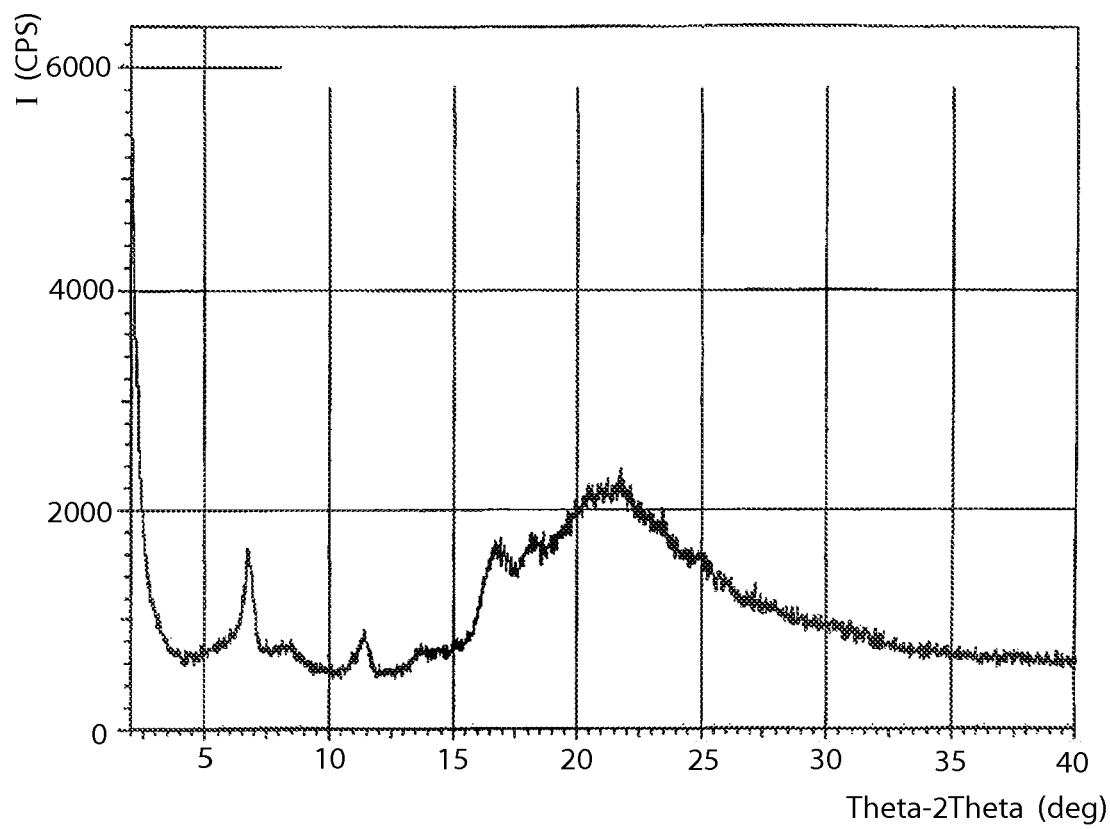
Figure 44:
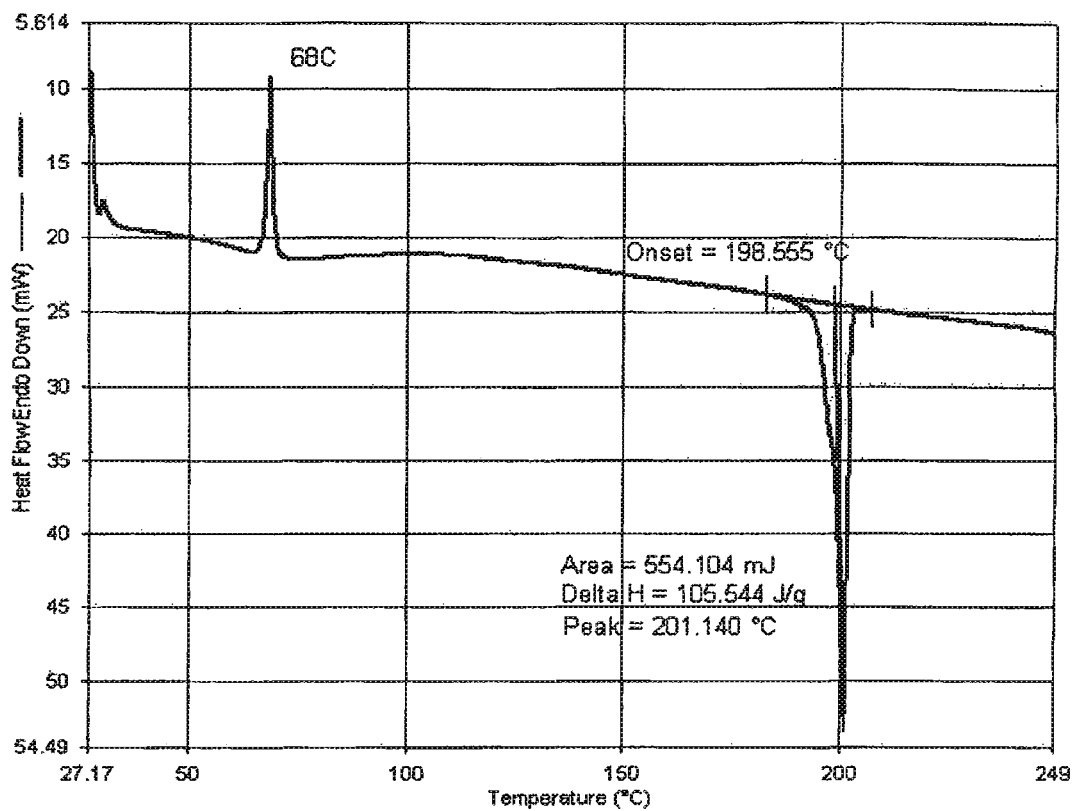
Figure 45:
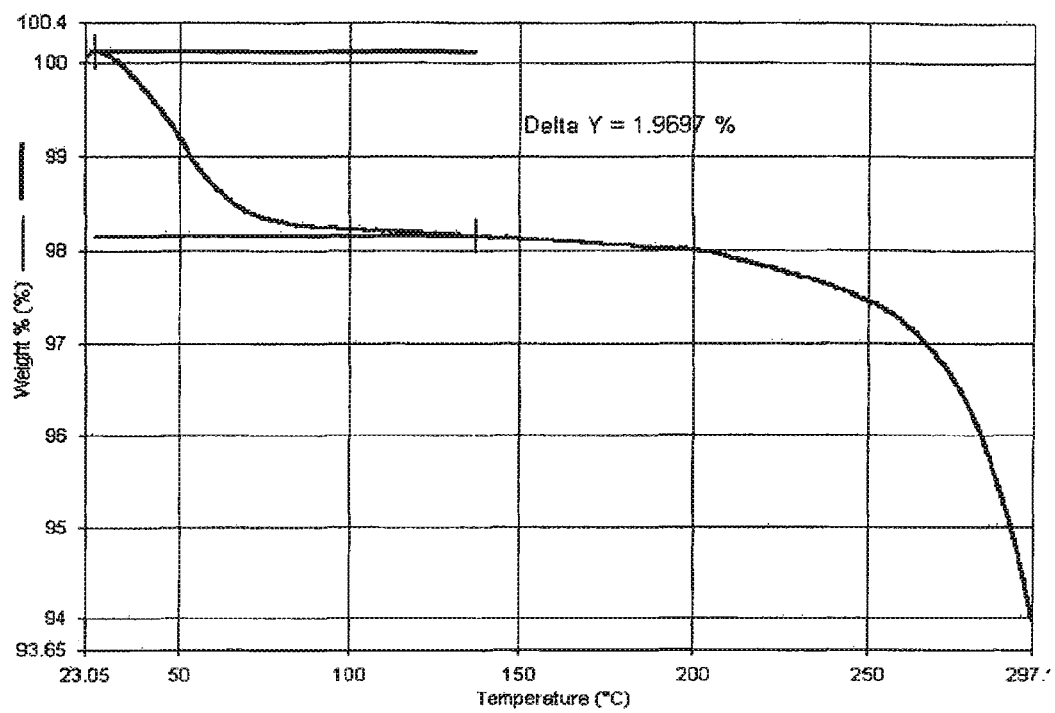
Figure 46:
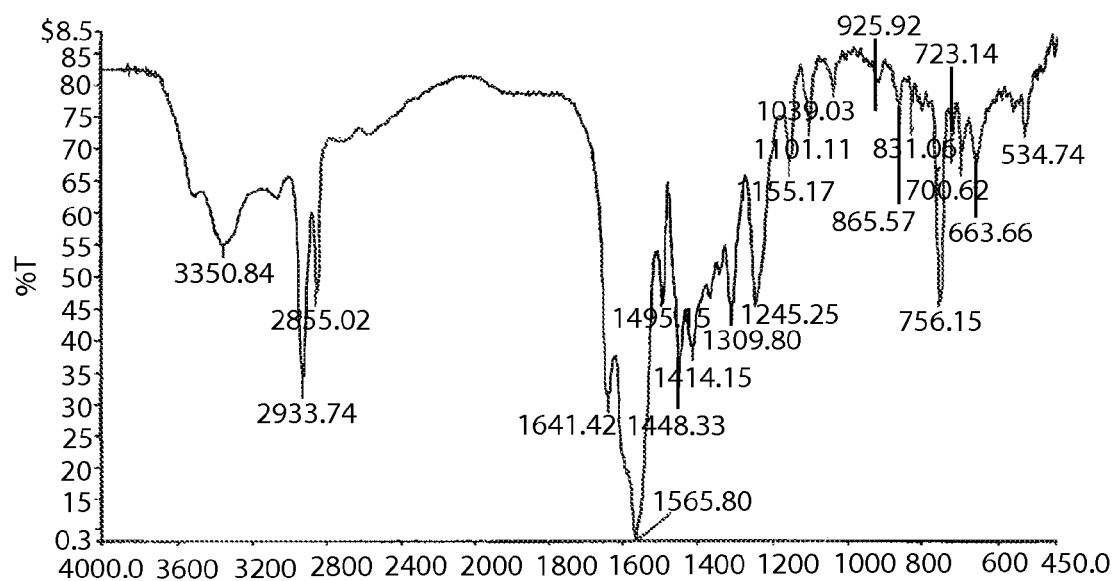
Figure 47:
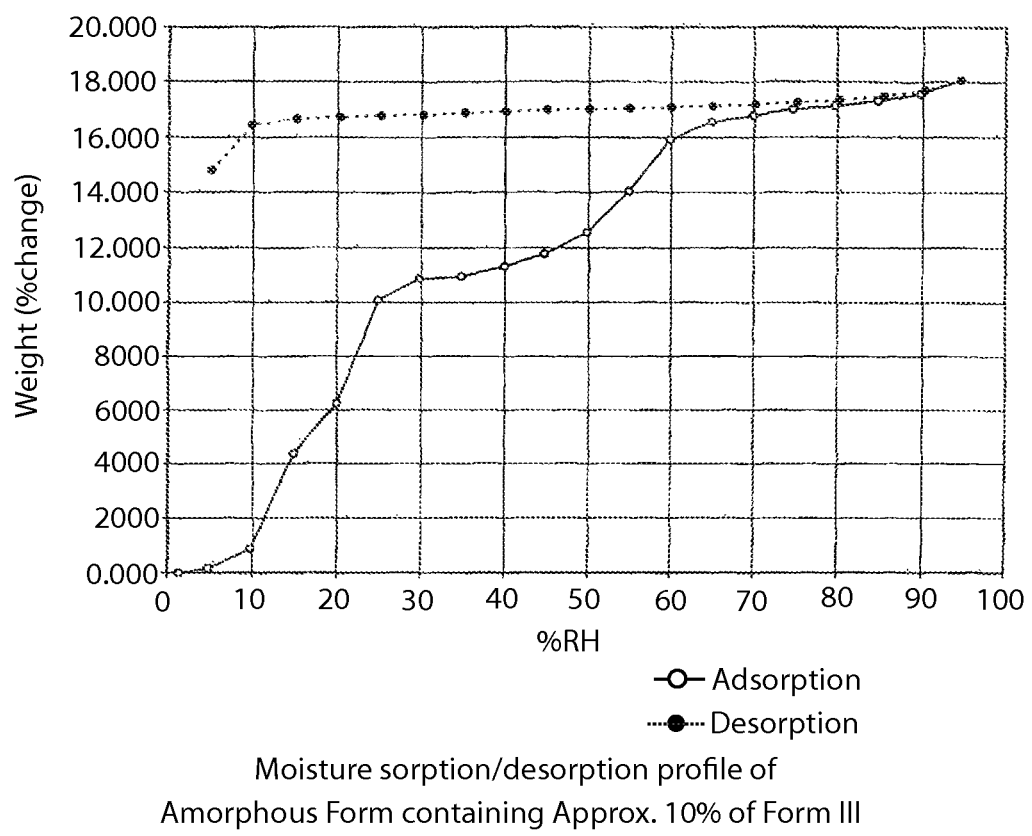

The results for Forms I and III are shown in FIGS. 41 and 42, respectively. As shown by these figure, the crystal form in both samples did not substantially change.

Example 14

Preparation of Amorphous SNAC

Amorphous form was prepared by drying Form III in a vacuum oven at 25° C. and 0.3 in. of Hg for 4 days. The dried material was a mixture of amorphous form and approximately 10% of initial Form III of SNAC. Longer drying and higher vacuum may result in substantially pure and pure amorphous form.

XRPD, DSC, TGA, FTIR, and sorption/desorption spectra for the amorphous SNAC containing approximately 10% of Form III are shown in FIGS. 43-47, respectively.

All patents, applications, articles, publications, and test methods mentioned above are hereby incorporated by reference.

We claim:

1. A method of preparing Form I of monosodium N-[8-(2-hydroxybenzoyl)amino]caprylate comprising
   (a) heating Form III, V, or VI of monosodium N-[8-(2-hydroxybenzoyl)amino]caprylate or a mixture thereof to at least 50° C. for a time sufficient to form Form I of monosodium N-[8-(2-hydroxybenzoyl)amino]caprylate;
   (b) heating amorphous monosodium N-[8-(2-hydroxybenzoyl)amino]caprylate at from about 30 to about 90° C. for a time sufficient to form Form I of monosodium N-[8-(2-hydroxybenzoyl)amino]caprylate; or
   (c) lyophilizing any form of monosodium N-[8-(2-hydroxybenzoyl)amino]caprylate other than Form I to yield Form I of monosodium N-[8-(2-hydroxybenzoyl)amino]caprylate.

2. The method of claim 1, wherein in step (a) the SNAC monosodium N-[8-(2-hydroxybenzoyl)amino]caprylate is heated to from about 50 to about 110° C. for a time sufficient to form Form I of monosodium N-[8-(2-hydroxybenzoyl)amino]caprylate.

3. The method of claim 1, wherein in step (b) the amorphous monosodium N-[8-(2-hydroxybenzoyl)amino]caprylate is heated at from about 40 to about 80° C.

4. The method of claim 1, wherein step (c) comprises lyophilizing one or more of Forms II-VI of monosodium N-[8-(2-hydroxybenzoyl)amino]caprylate and/or amorphous monosodium N-[8-(2-hydroxybenzoyl)amino]caprylate to yield Form I of monosodium N-[8-(2-hydroxybenzoyl)amino]caprylate.

5. A method of preparing Form II of monosodium N-[8-(2-hydroxybenzoyl)amino]caprylate comprising the step of drying a solvate of monosodium N-[8-(2-hydroxybenzoyl)amino]caprylate without agitation and exposing the dried monosodium N-[8-(2-hydroxybenzoyl)amino]caprylate to moisture for a sufficient time to yield Form II of SNAC monosodium N-[8-(2-hydroxybenzoyl)amino]caprylate.

6. The method of claim 5, wherein the solvate is an ethanol solvate or a methanol solvate.

7. A method of preparing Form III of monosodium N-[8-(2-hydroxybenzoyl)amino]caprylate comprising
   (a) exposing Form I, II, or IV of monosodium N-[8-(2-hydroxybenzoyl)amino]caprylate or amorphous monosodium N-[8-(2-hydroxybenzoyl)amino]caprylate or a mixture thereof to an environment having a relative humidity of 75% or greater for a sufficient time to yield Form III of monosodium N-[8-(2-hydroxybenzoyl)amino]caprylate;
   (b) wet granulating Form I of monosodium N-[8-(2-hydroxybenzoyl)amino]caprylate for a sufficient time to yield Form III of monosodium N-[8-(2-hydroxybenzoyl)amino]caprylate;
   (c) exposing Form V or VI of monosodium N-[8-(2-hydroxybenzoyl)amino]caprylate or a mixture thereof to an environment having a relative humidity of 30% or greater for a sufficient time to yield Form III of monosodium N-[8-(2-hydroxybenzoyl)amino]caprylate;
   (d) exposing Form VI of monosodium N-[8-(2-hydroxybenzoyl)amino]caprylate to an environment having a relative humidity of 10% or greater for a sufficient time to yield Form III of monosodium N-[8-(2-hydroxybenzoyl)amino]caprylate;
   (e) exposing amorphous monosodium N-[8-(2-hydroxybenzoyl)amino]caprylate to moisture for a sufficient time to yield Form III of monosodium N-[8-(2-hydroxybenzoyl)amino]caprylate; or
   (f) crystallizing monosodium N-[8-(2-hydroxybenzoyl)amino]caprylate from water to yield Form III of monosodium N-[8-(2-hydroxybenzoyl)amino]caprylate.

8. A method of preparing Form IV of monosodium N-[8-(2-hydroxybenzoyl)amino]caprylate comprising the step of heating Form I, II, III, V, or VI of monosodium N-[8-(2-hydroxybenzoyl)amino]caprylate or a mixture thereof to a temperature between about 110° C. and the melting point of monosodium N-[8-(2-hydroxybenzoyl)amino]caprylate for a sufficient time to yield Form IV of monosodium N-[8-(2-hydroxybenzoyl)amino]caprylate.

9. The method of claim 8, wherein the Form II of monosodium N-[8-(2-hydroxybenzoyl)amino]caprylate is heated to between about 150° C. and the melting point of monosodium N-[8-(2-hydroxybenzoyl)amino]caprylate for a sufficient time to yield Form IV of monosodium N-[8-(2-hydroxybenzoyl)amino]caprylate.

10. A method of preparing Form V of monosodium N-[8-(2-hydroxybenzoyl)amino]caprylate comprising
    (a) crystallizing monosodium N-[8-(2-hydroxybenzoyl)amino]caprylate from a methanol solution at a relative humidity of at least about 30% to yield Form V of monosodium N-[8-(2-hydroxybenzoyl)amino]caprylate;
    (b) equilibration of Forms I-IV or VI of monosodium N-[8-(2-hydroxybenzoyl)amino]caprylate with methanol to yield Form V of monosodium N-[8-(2-hydroxybenzoyl)amino]caprylate; or
    (c) slurrying any of Forms I-IV or VI of monosodium N-[8-(2-hydroxybenzoyl)amino]caprylate or a mixture thereof in methanol at a relative humidity of at least 30%, and maintaining the slurried mixture at ambient temperatures for a sufficient time to form Form V of monosodium N-[8-(2-hydroxybenzoyl)amino]caprylate.

11. The method of claim 10, wherein the methanol solution is substantially free of water.

12. The method of claim 10, wherein the equilibration in step (b) is performed in the absence of water.

13. A method of preparing Form VI of monosodium N-[8-(2-hydroxybenzoyl)amino]caprylate comprising
    (a) crystallizing monosodium N-[8-(2-hydroxybenzoyl)amino]caprylate from an ethanol solution at a relative humidity of at least about 30% to yield Form VI of monosodium N-[8-(2-hydroxybenzoyl)amino]caprylate;

(b) preparing a saturated solution of monosodium N-[8-(2-hydroxybenzoyl)amino]caprylate in ethanol at a relative humidity of at least about 30% and cooling the resulting solution to room temperature or lower to yield Form VI of monosodium N-[8-(2-hydroxybenzoyl)amino]caprylate; or (c) slurrying any of Forms I-IV of monosodium N-[8-(2-hydroxybenzoyl)amino]caprylate in ethanol at a relative humidity of at least about 30% to yield Form VI of monosodium N-[8-(2-hydroxybenzoyl)amino]caprylate.

14. The method of claim 13, wherein the ethanol solution in step (a) is substantially free of water.

15. The method of claim 13, wherein step (c) is performed in the absence of water.

16. A method of preparing amorphous monosodium N-[8-(2-hydroxybenzoyl)amino]caprylate comprising the step of dehydrating Form III, V, or VI of monosodium N-[8-(2-hydroxybenzoyl)amino]caprylate for a sufficient time to form amorphous monosodium N-[8-(2-hydroxybenzoyl)amino]caprylate.

17. The method of claim 16, wherein Form III, V, or VI of monosodium N-[8-(2-hydroxybenzoyl)amino]caprylate is dehydrated in a vacuum to form amorphous monosodium N-[8-(2-hydroxybenzoyl)amino]caprylate.

18. The method of claim 16, wherein Form III is dehydrated to form amorphous monosodium N-[8-(2-hydroxybenzoyl)amino]caprylate.

19. The method of claim 1, wherein the method comprises (a) heating Form III of monosodium N-[8-(2-hydroxybenzoyl) amino]caprylate or a mixture thereof to at least 50° C. for a time sufficient to form Form I of monosodium N-[8-(2-hydroxybenzoyl) amino]caprylate.

* * * * *